(12) United States Patent
Nishizawa

(10) Patent No.: US 7,912,553 B2
(45) Date of Patent: Mar. 22, 2011

(54) ELECTROMAGNETIC WAVE APPLICATOR

(75) Inventor: Jun-ichi Nishizawa, Miyagi (JP)

(73) Assignee: Jun-ichi Nishizawa, Sendai-shi (JP)

( * ) Notice: Subject to any disclaimer, the term of this patent is extended or adjusted under 35 U.S.C. 154(b) by 1550 days.

(21) Appl. No.: 10/536,878

(22) PCT Filed: Nov. 27, 2003

(86) PCT No.: PCT/JP03/15169
§ 371 (c)(1),
(2), (4) Date: May 27, 2005

(87) PCT Pub. No.: WO2004/047875
PCT Pub. Date: Jun. 10, 2004

(65) Prior Publication Data
US 2006/0113298 A1    Jun. 1, 2006

(30) Foreign Application Priority Data

Nov. 27, 2002  (JP) ................................ 2002-344483

(51) Int. Cl.
*A61F 7/00*  (2006.01)
*H05B 6/64*  (2006.01)

(52) U.S. Cl. .......................... 607/101; 607/102; 219/679

(58) Field of Classification Search .................... 607/96, 607/100–102; 250/341.1; 219/679, 748
See application file for complete search history.

(56) References Cited

U.S. PATENT DOCUMENTS

| | | | |
|---|---|---|---|
| 4,434,341 A | 2/1984 | Busby | |
| 5,052,408 A * | 10/1991 | Takase | 607/156 |
| 5,899,857 A * | 5/1999 | Wilk | 600/407 |
| 6,011,810 A * | 1/2000 | Haller et al. | 372/45.01 |
| 6,113,566 A * | 9/2000 | Schleicher | 604/6.08 |
| 6,144,679 A * | 11/2000 | Herman et al. | 372/21 |
| 6,329,136 B1 * | 12/2001 | Lagunas-Solar et al. | 435/2 |
| 6,448,850 B1 * | 9/2002 | Yamada | 330/44 |
| 6,461,351 B1 * | 10/2002 | Woodruff et al. | 606/32 |
| 6,479,822 B1 * | 11/2002 | Nelson et al. | 250/341.1 |
| 6,563,852 B1 * | 5/2003 | Baillargeon et al. | 372/45.01 |
| 6,719,716 B2 * | 4/2004 | Clark | 604/6.08 |
| 6,767,458 B2 * | 7/2004 | Safta | 210/202 |
| 6,991,927 B2 * | 1/2006 | Mross et al. | 435/173.1 |
| 2001/0049464 A1 | 12/2001 | Ganz | |

FOREIGN PATENT DOCUMENTS

DE    198 26 000 C1    12/1999

(Continued)

OTHER PUBLICATIONS

Mitsuru Musha, et al., "A Highly Stable mm-Wave Synthesizer Realized by Mixing Two Lasers Locked to an Optical Frequency Comb Generator", Science Direct, Optics Communications 240 (2004) 201-208.

*Primary Examiner* — Roy D Gibson
(74) *Attorney, Agent, or Firm* — Oblon, Spivak, McClelland, Maier & Neustadt, L.L.P.

(57) ABSTRACT

An electromagnetic wave irradiation tool encompasses a narrow tube (endoscope probe) (7) defined by an outside diameter of 0.1 mm-20 mm, having an electromagnetic wave irradiation terminal (3) configured to irradiate an electromagnetic wave (2) having a frequency equal to a characteristic frequency of a microorganism (11) at the top of the narrow tube (7) and an electromagnetic wave generation unit (3) configured to generate the electromagnetic wave (2) and to supply the electromagnetic wave (2) to the electromagnetic wave irradiation terminal (3). The electromagnetic wave irradiation tool drives the microorganism (11) into a resonant vibration state selectively so that the microorganism (11) can be destroyed, without giving damages to biological body (1) for medically treating the disease induced by the microorganism (11).

19 Claims, 13 Drawing Sheets

FOREIGN PATENT DOCUMENTS

| | | |
|---|---|---|
| JP | 63-249563 | 10/1988 |
| JP | 8-47528 | 2/1996 |
| JP | 11-196857 | 7/1999 |
| JP | 2000-245813 | 9/2000 |
| JP | 2001-231870 | 8/2001 |
| WO | 00/15097 | 3/2000 |
| WO | 00/78393 | 12/2000 |
| WO | WO 02/45790 A2 | 6/2002 |

* cited by examiner

HELICOBACTER PYLORI

ELECTROMAGNETIC WAVE APPLICATOR

BACKGROUND OF THE INVENTION

1. Field of the Invention

The present invention relates to an electromagnetic wave irradiation tool configured to irradiate an electromagnetic wave to a microorganism.

2. Description of the Related Art

Diseases, in which microorganisms such as bacteria or virus invades the human body from skin, mucous membrane, or body fluid of the human body so as to bring symptoms such as pyrexia, vomiting, and multiple organ failure in the human body, are known. Generally, these diseases are referred as "infectious diseases". As the microorganisms (causative agents) causing the infectious diseases, genus *staphylococcus*, genus *streptococcus*, family neisseria, genus *pseudomonas*, genus *legionella*, genus *brucella*, genus *bordetella*, genus *haemophilus*, genus *campylobacter*, genus *spirillum*, family intestinal bacteria, vibrio, genus *bacillus, lactobacillus, listeria* and *E. rhusiopathiae, obligate anaerobe*, genus *corynebacterium*, acid-fast bacterium, genus *mycobacterium*, genus *actinomyces* and *nocardia, spirochaeta, rickettsia, chlamydia*, etc. are known. These microorganisms break physical barrier lying in skin, mucous membrane, or body fluid, and invade in a biological host, and parasite to a tissue of the host. Because the microorganisms, being parasitic on the host, actively repeat multiplications, while producing toxins, an attack of toxin-induced inflammatory disease, which is developed by toxins produced in the living body, an attack of exudative inflammatory disease, which is developed by a rapid multiplication of the microorganisms in the infected site, and an attack of productive inflammatory disease, which is developed by sequential multiplications of the microorganisms at the target organ having an affinity with the microorganisms, etc. are found in the host.

For example, "*helicobacter pylori*" as shown in FIG. 14 is bacteria (causative agent) always existing on a mucous membrane of stomach of an animal. The "*helicobacter pylori*" is generally called as *pylori* bacteria, and the *pylori* bacteria produces an enzyme called urease in stomach so as to decompose urea into ammonia. When the generated ammonia is neutralized with a mucous membrane of stomach, the pylori bacteria lives stationary in stomach so as to establish a parasite state. As *pylori* bacteria continue multiplications in stomach, ammonia is produced excessively so as to cause damage of mucous membrane of stomach and excessive secretion of gastric acid, or alternatively to produce origins of gastric ulcer and gastric cancer, etc. It is said that malignant lymphoma growing in stomach is associated with bacteria such as *pylori* bacteria, in addition to Epstein-Barr (EB) viruses.

As counter-measures to medical treatment of the infectious disease, a methodology configured to prevent cell division of microorganisms by administering drugs to biological body so as to sterilize the microorganisms, which are parasitic on the biological body. For example, a chemotherapy configured to administer chemotherapy agent into living body, a serum therapy configured to inject immune serum into living body, and a vaccine therapy configured to inject vaccine such as antibiotics into living body, etc. are known.

There are microorganisms, to which effective treatment methods of the infectious disease due to the microorganisms are not found. For example, in July, 2002, a man of 69 years old has pricked his hand with a hook in the middle of fishing by mistake in Massachusetts, U.S.A., and bacteria called as "flesh-eating bacteria" were invaded to his body from a wound. Later, according to the Mainichi Shimbun newspaper of Aug. 10, 2002, this man noticed swelling of a finger at site where pricked with the hook two weeks after he had pricked his hand with the hook, the swelling of the finger has stretched over the whole arm in several hours, and is diagnosed as "necrotizing fasciitis" at a hospital. The doctor cut the finger, the hand, and the arm of the man in sequence in order to block the progress of a symptom, but the man has died by the infection one month later. In particular, the microorganism with which the man has been infected is a bacteria referred as "*photobacterium damsela*", with which the progress of the disease is extremely rapid among bacteria referred as "flesh-eating bacteria".

However, there is a problem in that a normal tissue of the host is damaged by drugs, which are administered so as to block the multiplication of the microorganisms for the counter-measure of the medical treatment of the infectious disease such as chemotherapy, serum therapy, or vaccine therapy, which are already discussed above. For example, in the case of above mentioned pylori bacteria, the sanitization in stomach is conducted by administering antimicrobial agent, which is mainly implemented by antibiotics. There is a problem of side effects such as diarrhea, hepatopathy, a renal insufficiency, because the antimicrobial agent acts on the normal tissue of the human body to which the antimicrobial agent is administered. There is another problem in which a new antimicrobial resistance appears against the antimicrobial agent.

Because the multiplication rate of microorganisms is extremely high, there is a case in which an appropriate medical treatment cannot suppress the multiplication rate for the infectious disease, which is induced by the microorganism and to which an effective medical treatment method is not established. Therefore, there are many cases that it is too late when an infectee noticed the symptom. For example, as for the infectious disease by "*photobacterium damsela*", when an infectee noticed the symptom such as swelling or pyrexia, the counter-measure of chemotherapy administering drugs were hardly effective, and there was no means to prevent effectively the multiplication of the microorganisms, which induce the symptom.

In view of these situations, it is an object of the present invention to provide an electromagnetic wave irradiation tool configured to destroy microorganisms such as bacteria or virus, by selectively exciting the microorganisms, without giving an effect to biological body.

SUMMARY OF THE INVENTION

In order to achieve the object, a first aspect of the present invention inheres in an electromagnetic wave irradiation tool encompassing a narrow tube defined by an outside diameter of 0.1 mm-20 mm, having an electromagnetic wave irradiation terminal configured to irradiate an electromagnetic wave having a frequency equal to the characteristic frequency of a microorganism at the top of the narrow tube, and an electromagnetic wave generation unit configured to generate the electromagnetic wave and to supply the electromagnetic wave to the electromagnetic wave irradiation terminal.

Although there are many kinds of microorganisms, the present invention mainly pertains to "causative agents (pathogenic microbes)". The "causative agents" are defined to be microorganisms harming a human being by invading into and multiplying in the human body, and includes bacteria, *Eumycetes* (molds), virus, protozoan. As is generally known, bacteria are classified into coccus (spherical-shaped bacteria), bacillus (cylindrical-rod-shaped bacteria), and spiral (helical-shaped bacteria) such as Leptospira. In the natural world, there are smaller microorganisms than bacteria. The microorganism having a size of 0.3 micrometer ordr is called as "rickettsia", less than or equal to 0.2 micrometer is called as "virus". In addition, the microorganism having an intermediate character between rickettsia and virus is called as "chlamydia".

Generally there are a plurality of characteristic frequencies for each of single microorganism. For example, in a lower frequency, the characteristic frequency of condensation chromosome in a cell is given by:

$$F\alpha = [k/(M/N)]^{1/2}/2\pi \tag{1}$$

Here, $F\alpha$ is the characteristic frequency of a condensation chromatid, k is a spring constant of the kinetochore-microtubule, M is molecular weight of the condensation chromatid, N is Avogadro's number ($=6\times10^{23}$). Because the molecular weight M of the condensation chromatid is about 60 billion grams/mole, and the spring constant k is $10^{-5}$, by substituting the values of M and k into Eq. (1), a value of $F\alpha=51.3$ kHz is obtained. In addition, a characteristic frequency around several MHz to around several hundreds MHz is obtained, with a diameter of the microorganism, a length of the microorganism, and a speed of sound in the microorganism, when the whole of the microorganism can be regarded as a system of a flexural vibration in a cantilever structure, as for the case of *helicobacter pylori*. Furthermore, many of the characteristic frequencies of molecule vibration by molecules composing a cell of a microorganism lie in a terahertz band. To be concrete, in bacteria of wild species, both in the shorter wavelength side and in the longer wavelength side of a spectrum, a rapid decay of 100 fs to 1 ps is observed in time domain, which correspond to the characteristic frequency of each terahertz band, respectively.

Generally, a microorganism (bacteria) has a cell membrane (cytoplasmic membrane) surrounding a cytoplasm, and there is a cell wall in the outside of the cell membrane. Here, let's focus on peptidoglycan composing the cell wall. As for this peptidoglycan, N-acetyleglucosamine (GlcNAC) and N-acetylmuramic acid (MurAC) couples alternately so as to implement β-1, 4 bond, forming a long glycan chain. An amino acid couples with a lactic acid residue of N-acetylemuramic acid so as to implement amide bond, forming peptide including four amino acids [L-Ala-D-Glu-DAP(Lys)-D-Ala]. Thus formed peptide implements a basic unit. Connecting several to dozens of the basic units, a long chain-shaped structure is established. In a cell wall, a plurality of glycan chains are running in parallel, bridging mutually between peptide chains so as to form a macromolecule. By species of bacteria (such as *staphylococcus*), a teichoic acid polymer is connected in the bridging structure of peptideoglycan. Because of this complex structure, there are various vibration modes in the macromolecule. Namely, depending on the structures of the molecule chain implementing the cell and the cell wall of a microorganism, there are a plurality of different characteristic frequencies. For example, the characteristic frequency of a bending vibration with three molecules is different from the characteristic frequency of a stretching vibration of five molecules. In this way, depending on modes of molecule vibrations by the molecules implementing the cell and the cell wall of a microorganism, there are various characteristic frequencies in terahertz band. Because the characteristic frequency of the macromolecule depends whether the vibration is a longitudinal mode or a transverse mode, or alternatively whether the vibration is the fundamental vibration or harmonics, there are many characteristic frequencies in a higher frequency region near terahertz band and in terahertz band.

In this way, according to the electromagnetic wave irradiation tool related to the first aspect of the present invention, electromagnetic waves from lower frequency region around dozens of kHz to higher frequency region around terahertz band can be employed. However, adjustment of frequency becomes complicated in the characteristic frequencies of the condensation chromatid and the flexural vibration, because these characteristic frequencies depend upon the actual sizes of microorganisms. On the other hand, because the characteristic frequencies of the molecule vibrations by the molecules composing cells of microorganism are the same for a specified kind of microorganism under the same boundary condition, the adjustment of frequency is easy. Therefore, in practical use, it is preferable to use electromagnetic waves having higher frequencies in terahertz band or near terahertz band.

According to the first aspect of the present invention, an electromagnetic wave irradiation terminal provided at the tip of the narrow tube emits an electromagnetic wave having a frequency equal to the characteristic frequency of a microorganism. Because the subject microorganism is excited selectively by the electromagnetic wave having a frequency equal to the characteristic frequency of the subject microorganism so as to establish a resonant vibration, only the subject microorganism becomes extinct, without giving damages to the cells around the subject microorganism. Therefore, infectious diseases ascribable to microorganisms can be treated effectively. A plurality of electromagnetic waves having different frequencies can be emitted simultaneously from the electromagnetic wave irradiation terminal, each of the different frequencies is same as each of the characteristic frequencies of the subject microorganism, so that the resonant vibration of the subject microorganism can be established, because the subject microorganism has a plurality of different characteristic frequencies. When the characteristic frequency of the microorganism varies due to the increase of temperature of the microorganism, because the energy of the electromagnetic wave is applied to the microorganism, the frequency of the electromagnetic wave may be controlled so as to follow the change of the characteristic frequency so that the resonant vibration state can be kept.

A second aspect of the present invention inhere in an electromagnetic wave irradiation tool encompassing an antenna-supporting member, an antenna provided on the antenna-supporting member, and an electromagnetic wave generation unit configured to supply an electromagnetic wave having a frequency equal to a characteristic frequency of a microorganism. The antenna may be implemented by a single antenna having a structure configured to employ an inner wall of the open-bell-shaped configuration such as a chest piece of a stethoscope, or alternatively by a combination of a plurality of antennas. The antenna-supporting member may be formed into a cylindrical geometry (cylinder) so that a body-to-be-irradiated can be inserted in the inside of the cylinder, and a plurality of patch antennas may be arranged to an inner wall of the cylinder so as to implement an antenna array. In this case, an electromagnetic wave, having a frequency equal to the characteristic frequency of a microorganism, is irradiated against the body-to-be-irradiated lying in the inside of the cylinder from the patch antennas provided on a wall surface of the antenna-supporting member.

According to the second aspect of the present invention, because only the subject microorganism is excited selectively by an electromagnetic wave having a frequency equal to the characteristic frequency of the subject microorganism (causative agent) so as to establish the resonant vibration, only the subject microorganism becomes extinct, without giving damages to the cells around the subject microorganism. Therefore, the microorganism, which has invaded in the surface of body-to-be-irradiated, is excited selectively so as to be killed. As already mentioned above, because there are a plurality of characteristic frequencies for a specified microorganism, it is preferable to use electromagnetic waves of terahertz band, especially to irradiate a plurality of electromagnetic waves having different frequencies, which are respectively equal to each of the characteristic frequencies, may be emitted from the antenna. Furthermore, as energy of the electromagnetic wave is absorbed so as to increase temperature of a microorganism, because the characteristic frequency of the microorganism varies due to the increase of the temperature, it is preferable to control the frequency of the electromagnetic wave so that the frequency of the electromagnetic wave can follow the variation of the characteristic frequency so as to keep the state of resonant vibration.

A third aspect of the present invention inheres in an electromagnetic wave irradiation tool encompassing a blood irrigation system having a blood-draw line configured to draw blood from a biological body and a blood-return line configured to return the blood to the biological body, an electromagnetic wave irradiation unit configured to irradiate an electromagnetic wave having a frequency equal to a characteristic frequency of a microorganism existing in the blood in the blood-draw line, and an electromagnetic wave generation unit configured to supply the electromagnetic wave to the electromagnetic wave irradiation unit.

According to the third aspect of the present invention, because the electromagnetic wave having the frequency equal to the characteristic frequency of the microorganism (causative agent) is irradiated to the blood, the microorganism produced in the blood is excited selectively so as to be driven into a resonant vibration state until the microorganism die. Because there are a plurality of characteristic frequencies for a specified microorganism, similar to the first and the second aspect, it is preferred to drive into the resonant vibration by an electromagnetic wave of terahertz band. In addition, electromagnetic waves having plural frequencies may be irradiated to the blood simultaneously. Furthermore, as the energy of the electromagnetic wave is absorbed so as to increase the temperature of the microorganism, because the characteristic frequency of the microorganism varies depending on the temperature, the frequency of the electromagnetic wave to be irradiated may be controlled so as to follow the change of the characteristic frequency so that the resonant vibration can be kept.

DETAILED DESCRIPTION OF THE INVENTION

Figure 1:
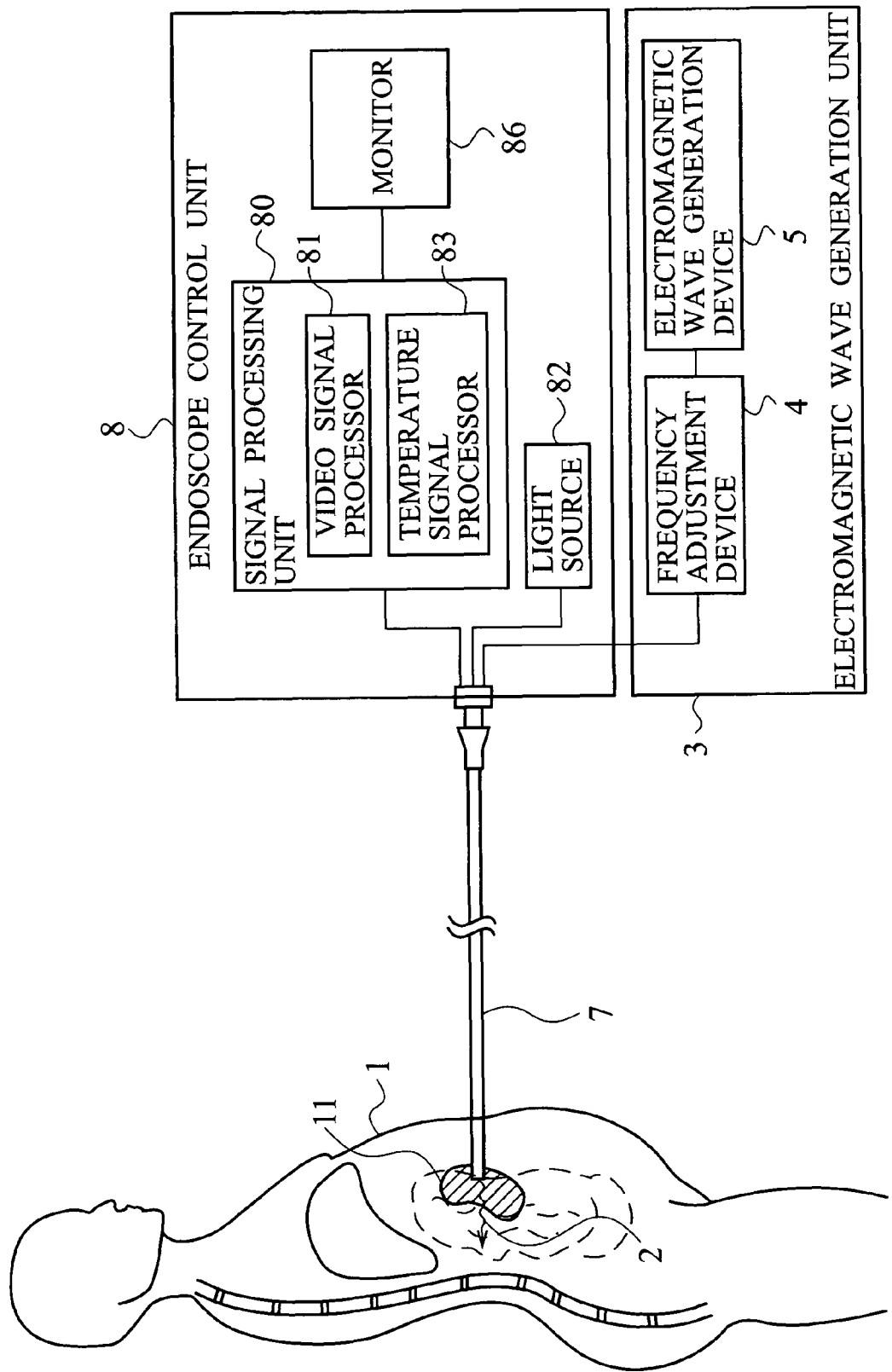
FIG. 1 shows a schematic illustration of an electromagnetic wave irradiation tool related to a first embodiment of the present invention.

The embodiments of the present invention will be described with reference to the accompanying drawings. It is to be noted that the same or similar reference numerals are applied to the same or similar parts and elements throughout the drawings. However the drawings are represented schematically, and it will be appreciated that the relationships between the layer thickness and the plane size, the proportions of thickness of each layer are different from the real configuration. In addition, the first to third embodiments represent examples of devices and methods to realize the technical idea of the present invention, and the technical idea of this invention is not limited to the materials of the constituent components, the geometry, the structure, the arrangement disclosed in the following discussion. Therefore, the technical idea of the present invention can be given various kinds of changes within the scope of claims.

First Embodiment

Figure 2:
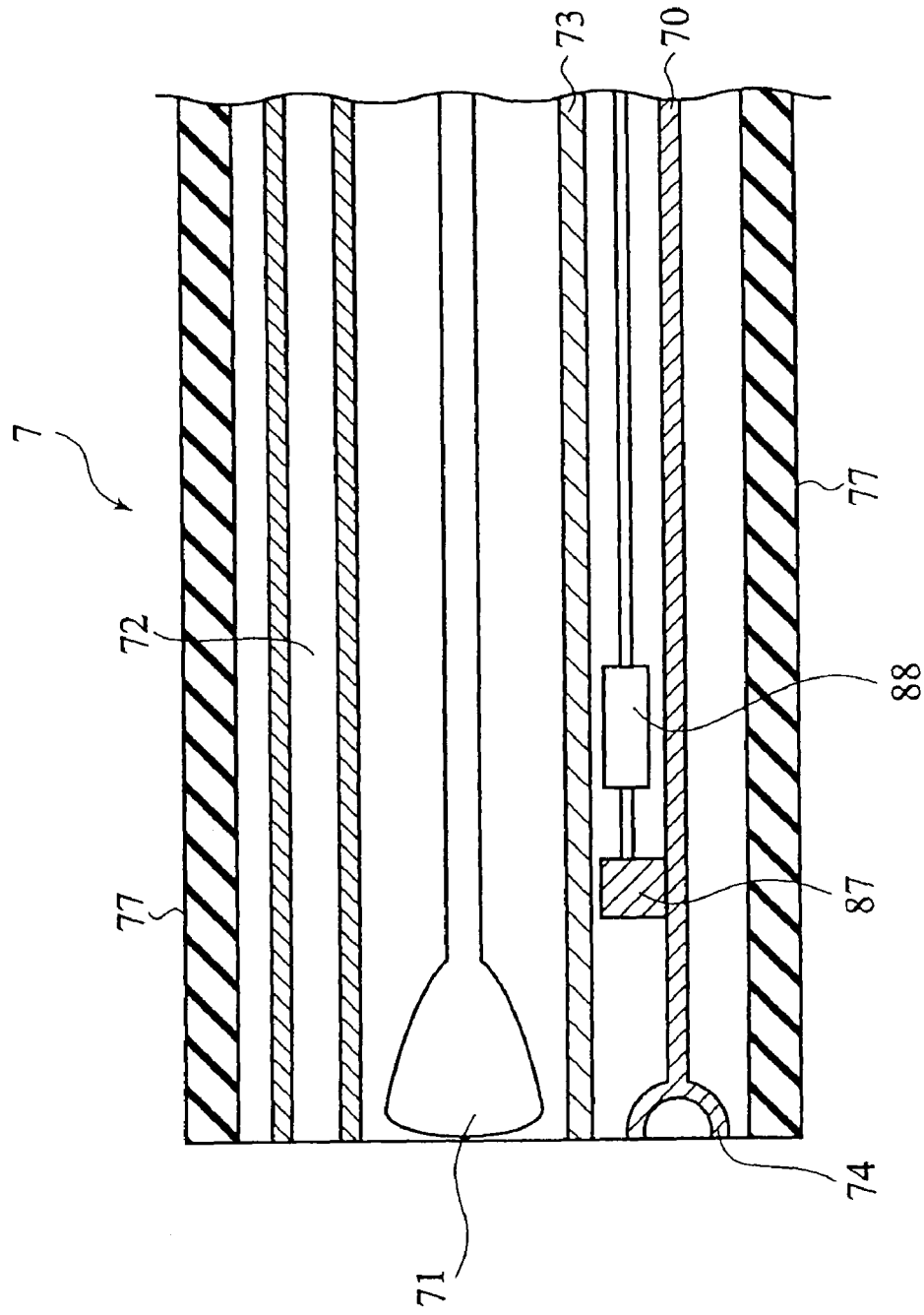
FIG. 2 shows a cross sectional view of an endoscope probe according to the first embodiment of the present invention.

As shown in FIGS. 1 and 2, an electromagnetic wave irradiation tool according to a first embodiment of the present invention is medical equipment, encompassing an electromagnetic wave generation unit 3 configured to generate an electromagnetic wave 2 having a frequency equal to the characteristic frequency (or "natural frequency") of a microorganism (causative agent) 11, and a narrow tube (endoscope probe) 7 having a 0.1 mm-20 mm outside diameter. The endoscope probe 7 has an electromagnetic wave irradiation terminal 74 configured to irradiate the electromagnetic wave 2 at the tip of the narrow tube. The narrow tube 7 further encompasses a light guide (optical waveguide) 72, configured to transmit light so that the light can irradiate the biological body, and a temperature detecting unit (a temperature-detecting terminal) 73 configured to detect temperature of the microorganism 11, as shown in FIG. 2. Although in FIG. 1, the narrow tube 7 is so represented that the narrow tube 7 can implement an endoscope probe 7, the narrow tube 7 can implements various structures such as a laparoscope employed in operations such as extirpation surgery of gallbladder (LAPAROSCOPIC CHOLECYSTECTOMY), a needle-shaped appliance (needle) employed in surgical operations of prostatic cancer, or a catheter configured to be inserted into a blood vessel or a body cavity. In addition, the outer diameter of the narrow tube 7 is so designed that a patient does not feel unpleasant by the presence of foreign substance (foreign body), and the outer diameter of the narrow tube 7 is preferable to be established around 0.1 mm-20 mm according to a size of a subject portion (surgical site) to which the medical surgery is applied. For example, an outer diameter of around 1 mm-10 mm is desirable for a surgery in which the narrow tube 7 is inserted in the digestive organs such as the large intestine or the small intestine, and when the narrow tube 7 is inserted from mouth, an outer diameter of around 10 mm-20 mm is preferable. Furthermore, for the laparoscope, an outer diameter of around 0.1 mm-15 mm is preferable.

Figure 3:
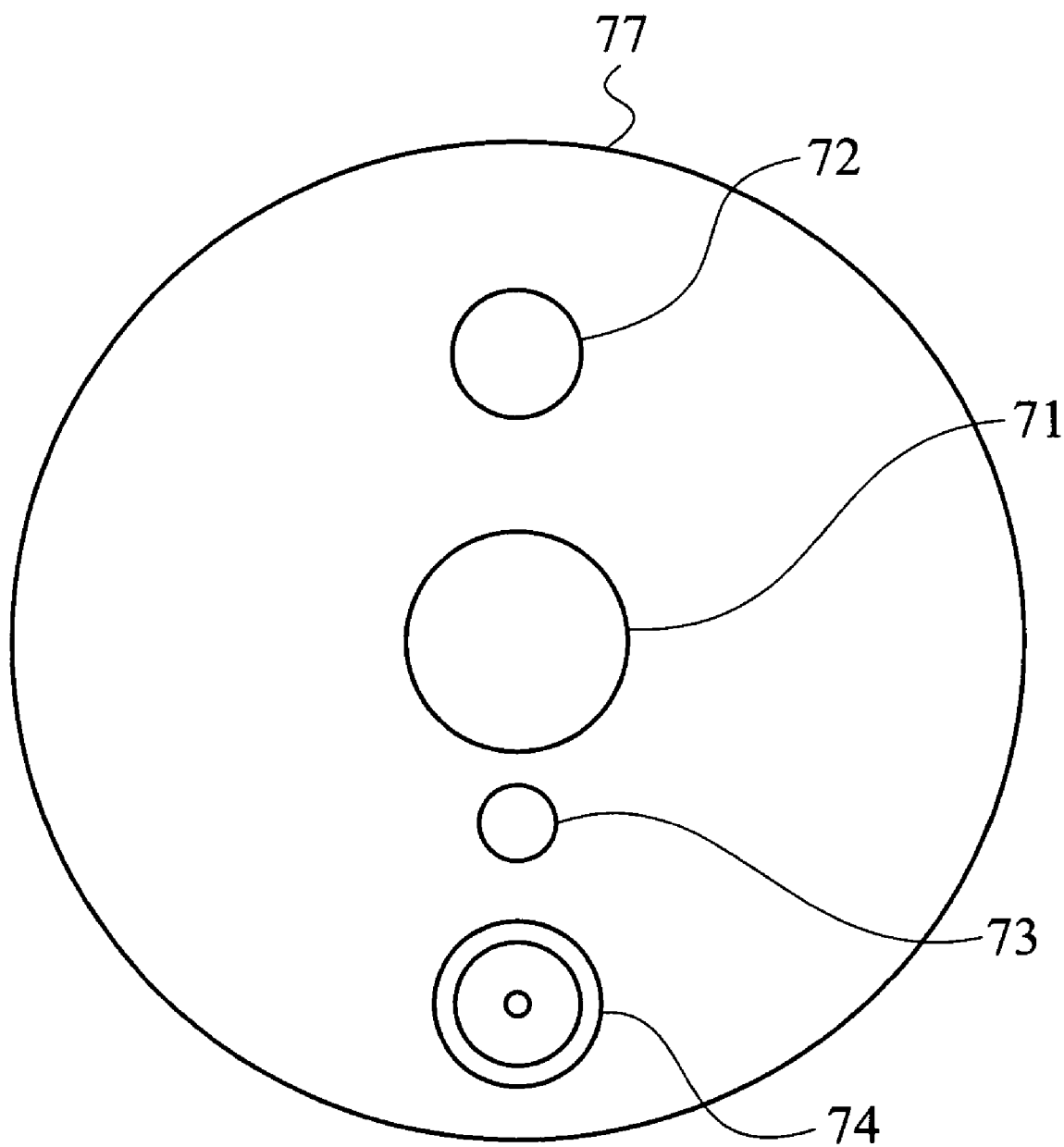
FIG. 3 is a schematic configuration showing a tip face of the endoscope probe according to the first embodiment of the present invention.

As shown in FIG. 2, the endoscope probe 7 has a CCD camera 71 configured to acquire internal picture information of the biological body, the CCD camera 71 is provided in a tubular shaft 77 to be inserted in the inside of biological body. The CCD camera 71, the light guide 72, the temperature-detecting terminal 73 and the electromagnetic wave irradiation terminal 74 are arranged in the tubular shaft 77 along a longitudinal direction. As illustrated in FIG. 3, each end face of the CCD camera 71, the light guide 72, the temperature-detecting terminal 73 and the electromagnetic wave irradiation terminal 74 comes into view at the tip face of the endoscope probe 7. Another end of the CCD camera 71, the light guide 72, the temperature-detecting terminal 73 and the electromagnetic wave irradiation terminal 74 are connected to an endoscope control unit 8 shown in FIG. 1. It is preferable that a CCD camera 71 has an object lens at one end face of the endoscope probe 7, the end face corresponds to the side to be inserted in the biological body. As for the light guide 72, an optical fiber of visible light can be used. The light guide 72 may transmit a picture image in addition to passing illumination light. That is to say, a beam splitter can separate a picture image transmitted through the light guide 72, and if a CCD camera acquires the picture information after the beam splitter has separated the picture image from the illumination light, the CCD camera 71 shown in FIG. 2 is unnecessary. In order to use the light guide 72 as a transmission line of picture information, the light guide 72 should be implemented by a so-called "self-focusing optical transmission line (graded index fiber)", in which axial distribution of refractive index establishes an paraboloidal-shaped distribution such that the refractive index is high at a central axis of the fiber and is low along the circumference region of the fiber. The temperature-detecting terminal 73 may be implemented by T type (Cu—Co) thermocouples, or alternatively, the temperature can be measured optically. When the temperature is measured optically, if material of the light guide 72 is chosen to be a light transmitting material of visible light and infrared light, the light guide 72 can serve as the temperature-detecting terminal 73. An antenna having a paraboloidal geometry or a horn geometry is preferred for the electromagnetic wave irradiation terminal 74. Furthermore, as the electromagnetic wave irradiation terminal 74, the tip of high frequency transmission line 70, which can transmit electromagnetic wave of terahertz band, such as a flexible hollow-tube light guide (light pipe) of a waveguide type, a coaxial cable, a microstrip line, a coplanar waveguide, can be employed.

In FIG. 3, although the CCD camera 71, the light guide 72, the temperature-detecting terminal 73 and the electromagnetic wave irradiation terminal 74 are aligned on a line, but it is not necessary to form the line topology, and any other arrangements can be adopted, of course. For example, if a coaxial cable is employed as the high frequency transmission line, a configuration such that the CCD camera 71, the light guide 72, the temperature-detecting terminal 73 are arranged in the inside of an insulation layer of the coaxial cable to surround a signal line of the coaxial cable, and the ground wiring is established at most outward side of the coaxial cable, can be adopted.

If frequency of the electromagnetic wave is higher than submillimeter band, a diameter of a flexible waveguide (hollow-tube light guide), serving as the high frequency transmission line 70, can be formed into equal to or smaller than 1 mm. The frequency of three THz corresponds to a wavelength of 0.1 mm in free air space. The electromagnetic wave irradiation terminal 74 may be a far infrared lens established at a tip of far infrared optical fiber as the high frequency transmission line 70. For the far infrared optical fiber, materials such as KRS-5 (TlBrI), TlBr, AgCl, AgBr, germanium oxide glass, fluorine glass can be employed. If the light guide 72 is formed of transparent materials transmitting from visible light to far infrared light such as diamond, or alternatively, is formed of a hollow-tube light guide (waveguide), the light guide 72 can serve simultaneously as the high frequency transmission line 70. Because a wavelength of high frequency electromagnetic wave in a medium is determined by a refractive index of materials implementing the far infrared optical fiber, a diameter of the far infrared optical fiber can be determined by the refractive index of material at the subject frequency.

When far infrared optical fiber is used, the light guide 72 can serve as the high frequency transmission line 70 and the temperature-detecting terminal 73, because the temperature can be measured optically through the light guide 72. In a neighborhood of the electromagnetic wave irradiation terminal 74, a variable stub 87 connected to the high frequency transmission line 70 is provided for impedance adjustment. The variable stub 87 is connected to the high frequency transmission line 70 through a micro actuator 88, and the micro actuator 88 drives the variable stub 87. Although detailed structure is not shown, the structure of the variable stub 87 may be determined by the structure of high frequency transmission line 70 such as a waveguide, a coaxial cable, a microstrip line, or a coplanar waveguide. If the light guide 72 is also used as a transmission line configured to transmit picture information, rather than using only the light guide 72 as a means for transmitting light for illumination light, as already mentioned above, the CCD camera 71 is unnecessary. Therefore, if the light guide 72 is formed of a wideband material through which spectrum from visible light to far infrared light can transmit entirely, the CCD camera 71, the high frequency transmission line 70, the temperature-detecting terminal 73 can be omitted in the configuration shown in FIG. 2. In particular, in such a simplified structure, outer diameter of the endoscope probe 7 can realize a value of less than or equal to 0.1 mm, when high frequency electromagnetic wave higher than three THz is used. Of course, even the endoscope probe having an outer diameter more than 0.1 mm can be employed. Because, at present, the outer diameter of the clad layer of marketed optical fiber is 0.125 mm (a diameter of core is 50 micrometers for a multi-mode, and ten micrometers for a single mode), an endoscope probe 7 having an outer diameter approximately same as the outer diameter of the clad layer may be fabricated theoretically, but if the structure shown in FIG. 2 is considered, equal to or larger than 0.2 mm is desirable for the outer diameter of the endoscope probe 7. In view of the easiness of manufacturing, equal to or larger than 0.5 mm is desirable for the outer diameter of the endoscope probe 7, but the upper limit of outer diameter is determined by requirement from medical care technology.

As shown in FIG. 1, the endoscope control unit 8 embraces a signal processing unit 80 connected to the CCD camera 71 and the temperature-detecting terminal 73, which are provided in the inside of the endoscope probe 7, a monitor 86 connected to the output side of signal processing unit 80, and a light source 82 connected to the light guide 72 provided in the inside of the endoscope probe 7. The signal processing unit 80 embraces a video signal processor 81 and a temperature signal processor 83. The video signal processor 81 and the temperature signal processor 83 can use a picture image analyzer and a temperature measuring apparatus, respectively. As for the light source 82, a visible semiconductor laser, a visible light emitting diode (LED), a discharge tube, a fluorescence lamp can be used. The visible semiconductor laser and the visible LED may be provided at the tip of the endoscope probe 7. As to the visible semiconductor laser and the visible LED, three colors of R (red), G (green) and B (blue) are mixed to emit a white light, or the wavelength of the light emitted from the visible semiconductor laser or the visible LED my be adjusted to a value with which the microorganism 11 can be identified most efficiently.

Figure 4:
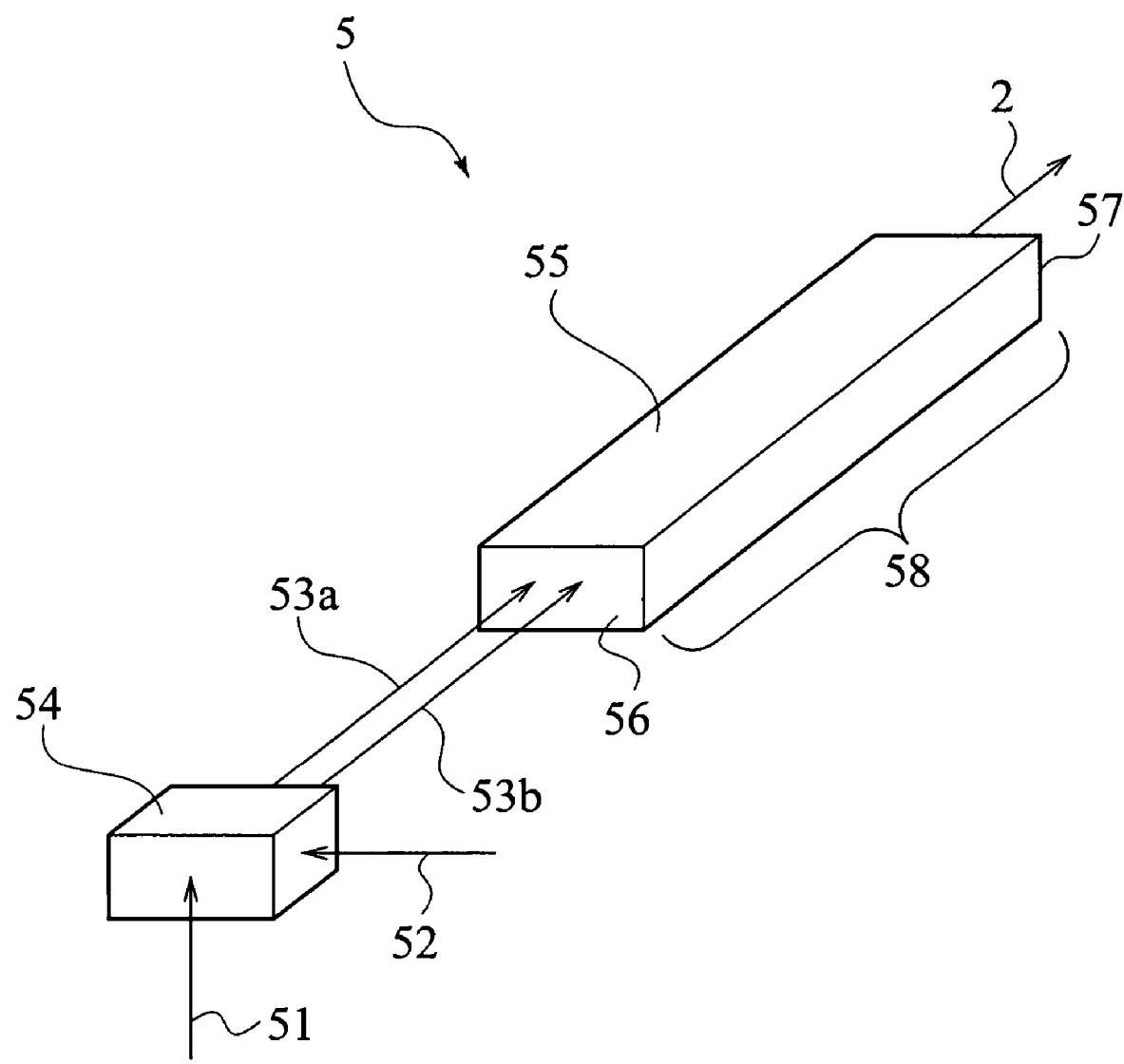
FIG. 4 shows a schematic illustration of an electromagnetic wave generation device according to the first embodiment of the present invention.

The electromagnetic wave generation unit 3 is a means for generating a specific electromagnetic wave having a frequency equal to the characteristic frequency of a subject microorganism 11 so as to drive the subject microorganism 11 into a resonant vibration state, by selecting the frequency equal to the characteristic frequency. For example, as shown in FIG. 1, the electromagnetic wave generation unit 3 embraces a relatively wideband electromagnetic wave generation device 5 configured to generate a electromagnetic wave 2 having a frequency equal to the characteristic frequency of a subject microorganism 11, and a frequency adjustment unit (frequency adjustment device) 4 configured to adjust the frequency of the electromagnetic wave to be irradiated on the subject microorganism 11 so as to follow a change of characteristic frequency of the subject microorganism 11. In this case, a semiconductor non-linear optical device is used for the frequency adjustment device 4. The electromagnetic wave generation device 5 may use a terahertz band electromagnetic wave generation device configured to extract the difference frequency of two pumping lights, as shown in FIG. 4, for example. To be concrete, as shown in FIG. 4, an electromagnetic wave generation device 5 encompassing a pumping light control member 54 configured to emit synthesizing beams 53a and 53b, after receiving a first pumping light 51 and a second pumping light 52 incident on the pumping light control member 54; and an electromagnetic wave generation member 55 configured to emit an electromagnetic wave 2 having a frequency equal to a difference between the frequency of the first pumping light 51 and the frequency of the second pumping light 52, after receiving the synthesizing beams 53a and 53b, which strike perpendicularly to an entrance end face 56, can be used. The first pumping light 51 and the second pumping light 52 can be emitted from light sources such as a single mode laser diode, a distributed feedback (DFB) semiconductor laser and a wavelength tunable semiconductor laser encompassing a resonator and a diffraction grating. As the pumping light control member 54, a polarizing beam splitter can be used. The electromagnetic wave generation member 55 encompasses the entrance end face 56, an exit end face 57 opposite to the entrance end face 56, and an optical waveguide 58 located between the entrance end face 56 and the exit end face 57. A single crystal having a crystal orientation specified by a specific Miller index may be elected so that the crystal orientation can define the propagation direction of the optical waveguide 58. $SiO_2$—$TiO_2$ multilayer evaporation films are coated on the entrance end face 56 and the exit end face 57. The optical waveguide 58 is a ridge type optical waveguide encompassing a GaP core layer and clad layers formed of $Al_xGa_{1-x}P$ layer, the clad layers are arranged in circumference of the GaP core layer. As an optical waveguide 58, materials such as zinc telluride (ZnTe) or lithium niobate ($LiNbO_3$) may be used.

In the electromagnetic wave generation device 5 shown in FIG. 4, the first pumping light 51 and the second pumping light 52 are incident on the pumping light control member 54 at first. Next, the first pumping light 51 and the second pumping light 52 incident on the pumping light control member 54 are synthesized by a polarizing beam splitter so as to form synthesizing beams 53a and 53b, which are incident on the entrance end face 56 of electromagnetic wave generation member 55. When the synthesizing beams 53a and 53b are incident on the GaP core layer from the entrance end face 56, the difference-frequency light coupled with TO phonon is excited, and an electromagnetic wave 2 having a frequency equal to the difference between the first frequency and the second frequency is emitted from the exit end face 57.

In addition, as another examples, other than the electromagnetic wave generation device 5 shown in FIG. 4, various electromagnetic wave generation devices generating electromagnetic waves between millimeter wave band and far infrared band such as electron tubes including a magnetron, a traveling-wave tube and a klystron, and gas lasers including an $H_2O$ laser, an $O_2O$ laser, a HCN laser, a DCN laser are preferable. Furthermore, terahertz band solid-state oscillators superior in features such as small size, lightweight, low operation voltage and low power dissipation in comparison with the electron tubes or the gas lasers, can be employed, too. But, in a resonator using the solid-state oscillators, the output deteriorates if frequency becomes high, the noise characteristic becomes significant and frequency becomes unstable. Conditions of a resonator for solid oscillators for solving the problems of increased noise characteristic and frequency instability are: (1) the resonator has a high Q value; (2) the resonator has a structure configured to facilitate a synchronized oscillation and power combining schemes; and (3) the size of the resonator is larger than wavelength. As a terahertz band electromagnetic wave generation device 5 satisfying such conditions, an oscillator implemented by a quasi-optical resonator can be employed. For example, terahertz band oscillators such as a Gunn diode, a TUNNETT diode and an ideal SIT, using a quasi-optical Fabry-Perot resonator embracing a concave mirror and a diffraction grating, may implement the synchronized oscillation and the power combining schemes. If a wavelength tunable electromagnetic wave generation device 5 such as a spin-flip Raman laser is used for the electromagnetic wave generation unit 3, the frequency adjustment device 4 can be omitted. If a plurality of electromagnetic wave generation devices 5 are prepared in correspondence with plural frequency ranges, the frequency band by which the electromagnetic wave generation unit 3 covers may be magnified as a result. In addition, as already explained, because a plurality of characteristic frequencies of the subject microorganism 11 may exist in each of a specified microorganism 11, a plurality of electromagnetic wave generation devices 5 may be prepared for each of characteristic frequencies so that a plurality of electromagnetic waves having different frequency can be irradiated simultaneously on the subject microorganism 11. In correspondence with plural electromagnetic wave generation devices 5, a plurality of frequency adjustment devices 4 are provided respectively.

Next, a procedure of medical treatment using the electromagnetic wave irradiation tool according to the first embodiment of the present invention will be described with reference to FIGS. 1 to 5.

(a) At first, a site of the subject microorganism 11 in the body of a patient is specified. To be concrete, after puncturing the biological body 1 via a trocar (not shown), the endoscope probe 7 is inserted percutaneously in the biological body 1 as shown in FIG. 1. The endoscope probe 7 may be inserted from mouth of the biological body 1. Next, the light emitted from the light source 82 is irradiated through the light guide 72 shown in FIG. 2 from the tip of the endoscope probe 7, a picture image around the tip the endoscope probe 7 is acquired. The picture image is acquired by the CCD camera 71, and analyzed by the video signal processor 81 shown in FIG. 1, and displayed on the monitor 86. In addition, the picture image displayed on the monitor 86 should be processed so that the identification of the subject microorganism 11 becomes easy, by emphasizing only a specific color. For example, it is preferable to execute IHb color enhancement process or mucous membrane homodynamics image process for representing a specific color more distinctly. Or, like a laser microscope, the subject microorganism 11 can be easily specified, by irradiating laser light of a specific color from a semiconductor laser.

Figure 5:
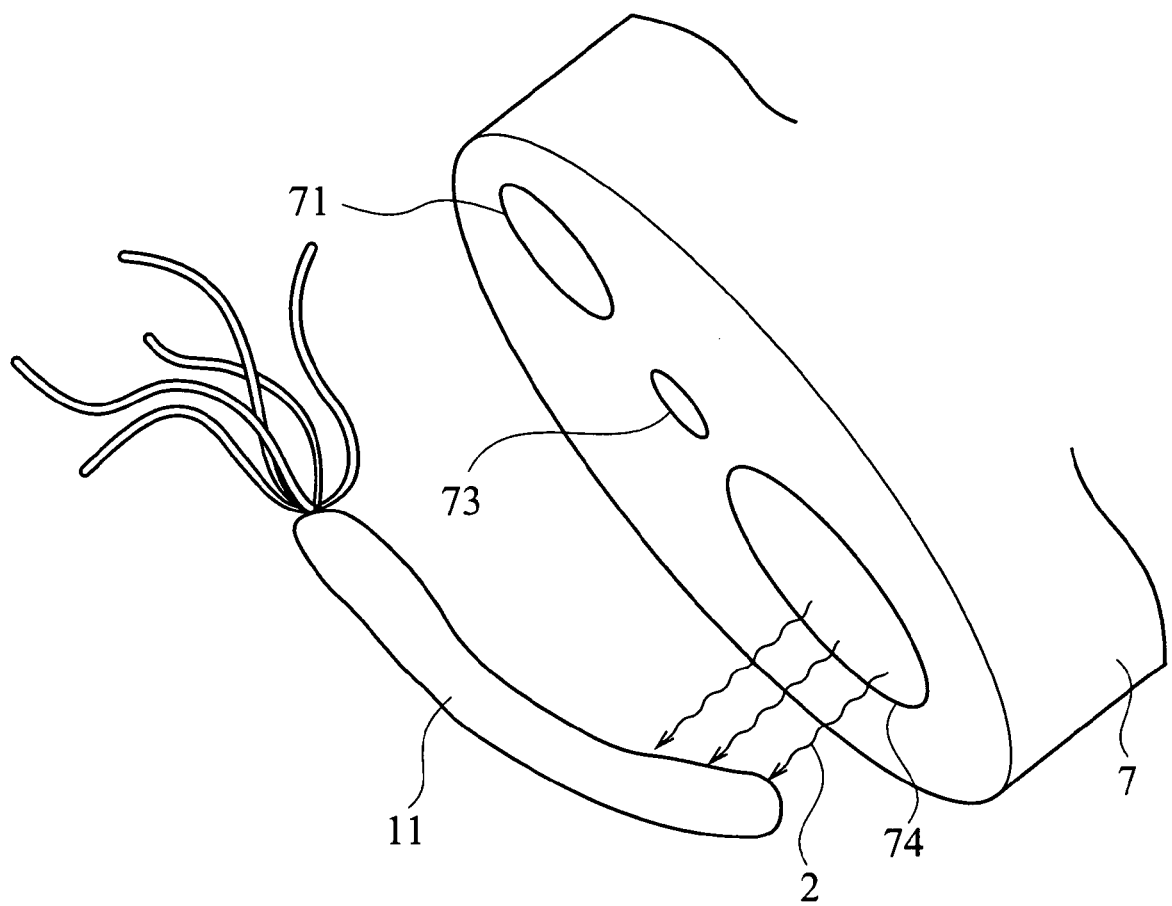
FIG. 5 is a schematic configuration showing a medical treatment method, using an electromagnetic wave irradiation tool according to the first embodiment of the present invention.

(b) Next, while observing a picture image on the monitor 86 so as to confirm the existing site of the subject microorganism 11, as shown in FIG. 5, the tip of the endoscope probe 7 is brought close to the subject microorganism 11. And the temperature-detecting terminal 73 and the electromagnetic wave irradiation terminal 74 are forced to approach the subject microorganism 11. Temperature information of the subject microorganism 11 is detected by the temperature-detecting terminal 73, after the temperature information is analyzed by the temperature signal processor 83 shown in FIG. 1, the temperature information is displayed on the monitor 86. Next, an electromagnetic wave 2 is generated by the electromagnetic wave generation device 5, the frequency of the electromagnetic wave 2 is adjusted so that the frequency of the electromagnetic wave 2 is equal to the characteristic frequency of the subject microorganism 11 by the frequency adjustment device 4. It is preferable that the electromagnetic wave 2 having the frequency equal to the characteristic frequency of the subject microorganism 11 is determined beforehand by Raman scattering spectrometry. It is preferable that, before medically treat the subject microorganism 11, which is parasitic on a patient, the subject microorganism 11 is picked beforehand so as to measure the characteristic frequency. The characteristic frequency may be determined by the measurement of the standing wave ratio (VSWR) of the electromagnetic wave 2 irradiated on the subject microorganism 11, which will be measured by a reflection-factor measuring instrument. Or a pulse wave is irradiated to the subject microorganism 11 so as to determine the characteristic frequency by the frequency response measurement. Furthermore, by in-situ monitoring through a microscope, in which a picture image representing the change of the subject microorganism 11 is transmitted through the light guide 72, under the condition such that electromagnetic waves 2 are irradiated on the subject microorganism 11, the characteristic frequency can be specified.

(c) Next, for example, an electromagnetic wave 2 of 1.5 THz to 100 THz is irradiated to the subject microorganism 11 from the electromagnetic wave irradiation terminal 74 provided at the tip of the endoscope probe 7, as shown in FIG. 5, so as to drive the subject microorganism 11 into resonant vibration state. At this time, the variable stub 87 is driven by the micro actuator 88 so as to adjust the terminal impedance of the high frequency transmission line 70, and power of the electromagnetic wave 2 is irradiated on the subject microorganism 11. Although FIG. 5 shows a *helicobacter pylori* as an example of the subject microorganism 11, the other microorganisms can be employed as the subject microorganism 11, of course. Because the *helicobacter pylori* to which an electromagnetic wave 2 is irradiated is excited by energy of the electromagnetic wave 2 to become a resonant vibration state, a cell membrane or a flagellum of the *helicobacter pylori* oscillates greatly. The *helicobacter pylori* being oscillated greatly by the resonant vibration is extirpated finally, because the cell is destroyed. In addition, because kinetic energy of the subject microorganism 11 increases by the irradiation of the electromagnetic wave 2, temperature of the subject microorganism 11, to which the electromagnetic wave 2 irradiated, rises. Therefore, nature of the temperature dependence of the change of characteristic frequency of the subject microorganism 11 is measured beforehand. And, based upon the temperature data detected by the temperature-detecting terminal 73, it is preferable to determine the frequency of the electromagnetic wave 2 to be irradiated, and to adjust the frequency of the electromagnetic wave 2 by the frequency adjustment device 4. In addition, it is desirable to adjust the impedance of the high frequency transmission line 70 by the variable stub 87, which is driven by the micro actuator 88, because the terminal impedance of the high frequency transmission line 70 varies with the change of frequency ascribable to the temperature change. Because the behavior of the subject microorganism 11 can be grasped directly through the in-situ monitoring on the monitor 86, by observing a change of movement of the subject microorganism 11, the resonance state of the subject microorganism 11 can be obtained so that the frequency of the electromagnetic wave 2 to be irradiated can be changed appropriately by the frequency adjustment device 4. In addition, because a plurality of characteristic frequencies may be inherent in the subject microorganism 11, from the electromagnetic wave generation unit 3, electromagnetic waves 2 having a plurality of frequencies different from each other may be supplied through the electromagnetic wave irradiation terminal 74 simultaneously so as to be irradiated on the subject microorganism 11, the different frequencies of the electromagnetic waves 2 corresponding to the different characteristic frequencies of the subject microorganism 11, respectively.

According to the electromagnetic wave irradiation tool related to the first embodiment of the present invention, by establishing the resonant vibration in the subject microorganism 11, because only the subject microorganism 11 in the body of a patient is destroyed selectively, the progress of a certain infectious disease associated with microorganism 11 can be blocked effectively.

Modification of the First Embodiment

Figure 6:
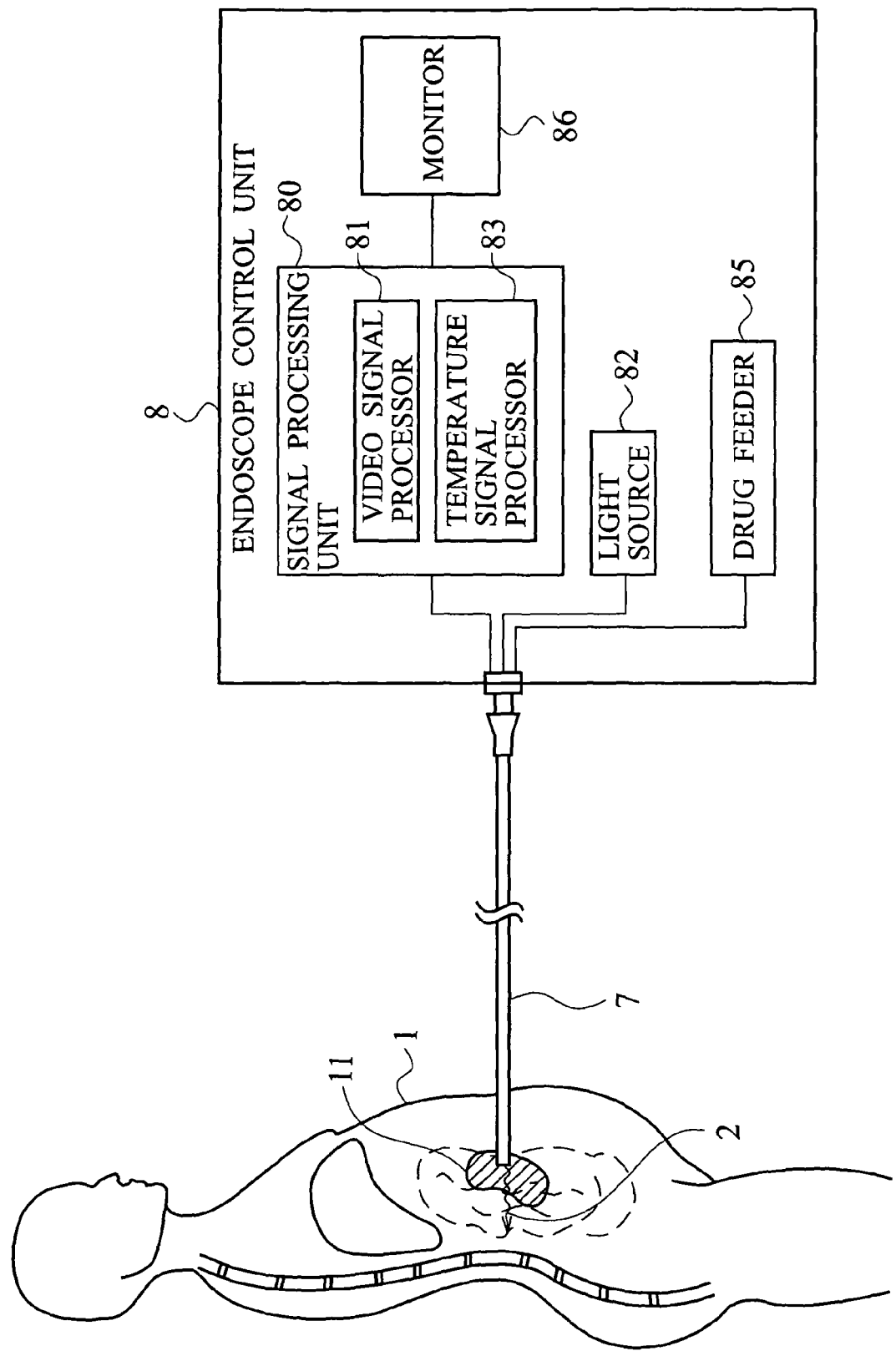
FIG. 6 shows a schematic illustration of an electromagnetic wave irradiation tool according a the modification of the first embodiment of the present invention.
Figure 7:
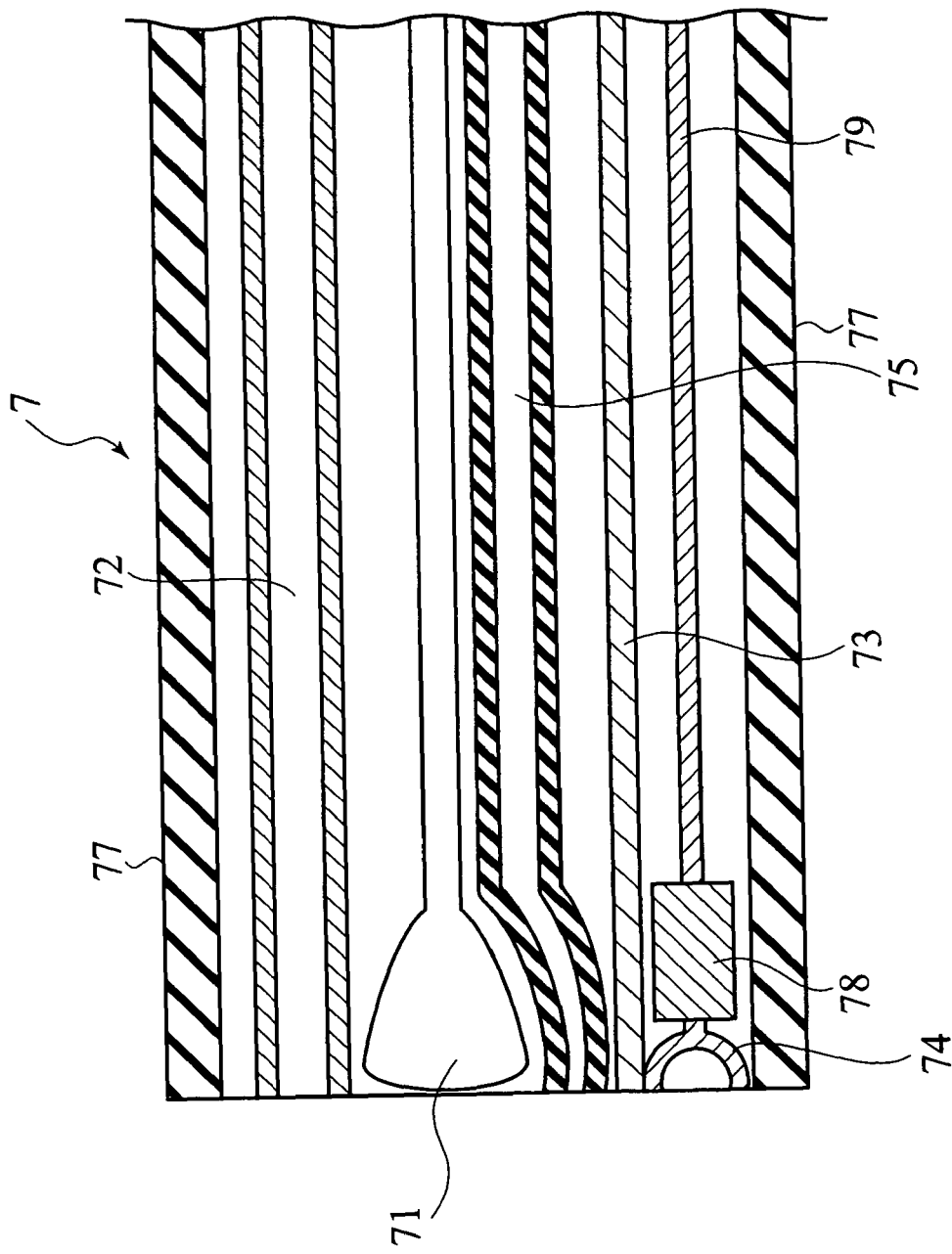
FIG. 7 shows a cross sectional view of an endoscope probe according to the modification of the first embodiment of the present invention.
Figure 8:
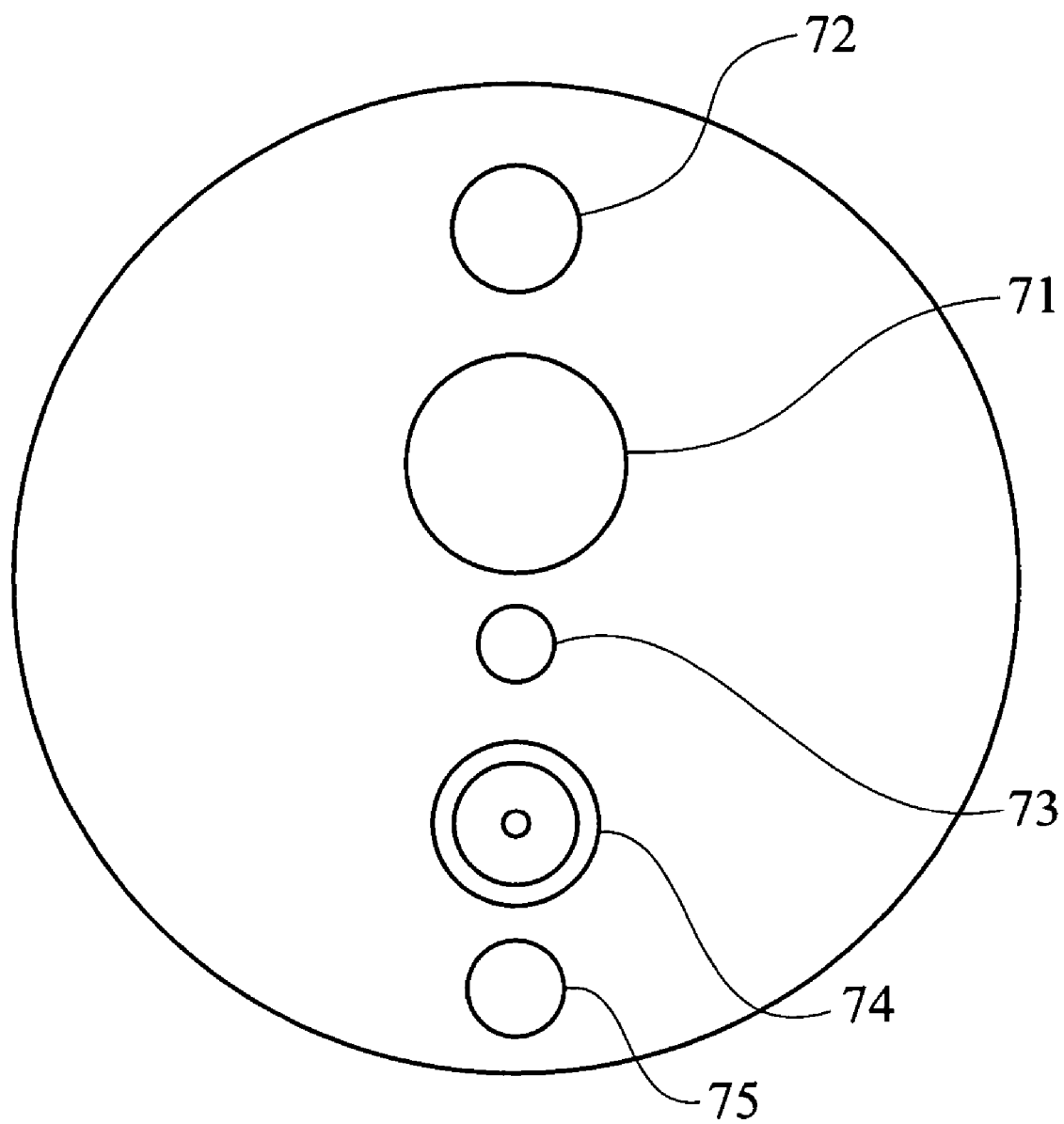
FIG. 8 is a schematic configuration showing a tip face of the endoscope probe according to the modification of the first embodiment of the present invention.

As shown in FIGS. 7 and 8, an electromagnetic wave irradiation tool according to a modification of the first embodiment of the present invention is different from the electromagnetic wave irradiation tool shown in FIGS. 1 to 3 in a feature that the electromagnetic wave irradiation tool encompasses a drug injection tube 75 disposed in the inside of the endoscope probe 7, which is aligned in parallel with the CCD camera 71, the light guide 72, the temperature-detecting terminal 73 and the electromagnetic wave irradiation terminal 74, and a monolithic integrated circuit 78 provided at the internal tip side of the endoscope probe 7 so as to connect with the electromagnetic wave irradiation terminal 74. Furthermore, as shown in FIG. 6, the electromagnetic wave irradiation tool according to the modification of the first embodiment is different from the electromagnetic wave irradiation tool shown in FIGS. 1 to 3 in that a drug feeder 85 is connected to the drug injection tube 75.

The monolithic integrated circuit 78 shown in FIG. 7 operates as the terahertz band electromagnetic wave generation unit 3. Direct current bias and necessary signals are supplied the monolithic integrated circuit 78 through a power supply wiring 79. It is preferable that the monolithic integrated circuit 78 encompasses a relatively wideband amplification circuit and a frequency tuner, adapted for generating electromagnetic waves 2 having frequencies equal to the characteristic frequencies of the subject microorganism (causative agent) 11. Terahertz band amplifier, oscillator (active semiconductor elements) such as ideal SIT can be used for the monolithic integrated circuit 78. The drug injection tube 75 injects the drug supplied by the drug feeder 85 into the tissue where the subject microorganism 11 is parasitic on. As the drug to be injected, drugs or medicines for promoting nutrition, depending on kinds of the subject cells, can be employed. For example, a photosensitive material such as porfimer sodium, which is employed in photo dynamic diagnosis (PDD) or photo dynamic therapy (PDT), is preferred so that the subject microorganism 11 such as bacteria can emit fluorescence light so as to facilitate specifying the location of the subject microorganism 11.

In FIG. 8, although the CCD camera 71, the light guide 72, the temperature-detecting terminal 73 and the electromagnetic wave irradiation terminal 74, the drug injection tube 75 are aligned on a line, it is not necessary to be aligned on a line, and other topologies can be adopted, of course.

According to the modification of the first embodiment of the present invention, the subject microorganism 11 is easily specified, as the drug such as photosensitive materials is injected into the biological body 1. If a drug having a sterilization effect against the subject microorganism 11 is injected, the destruction effect to the subject microorganism 11 by the irradiation of the electromagnetic wave 2 can be increased more.

Second Embodiment

Figure 9:
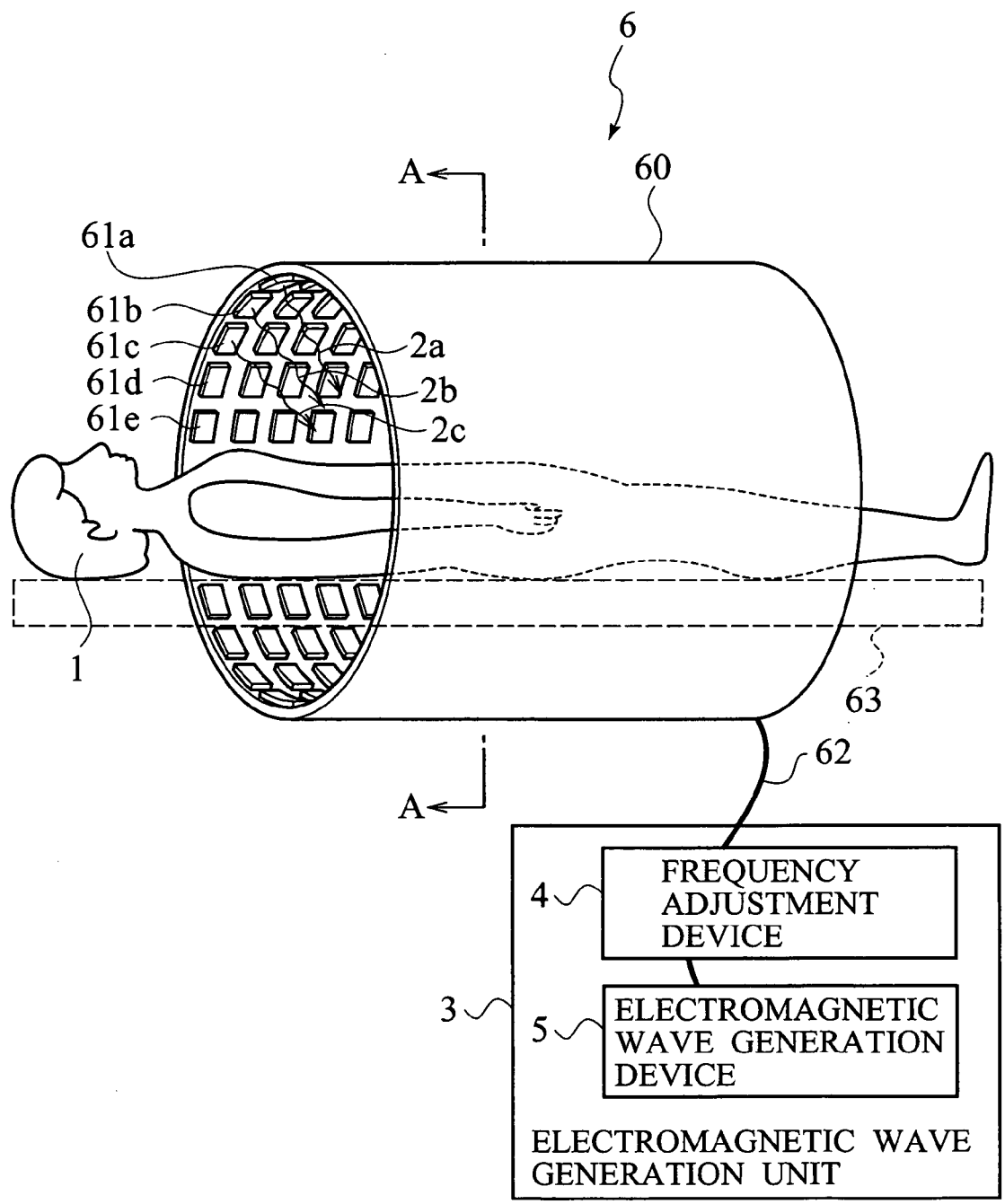
FIG. 9 is a schematic configuration showing an electromagnetic wave irradiation tool according to a second embodiment of the present invention.
Figure 10:
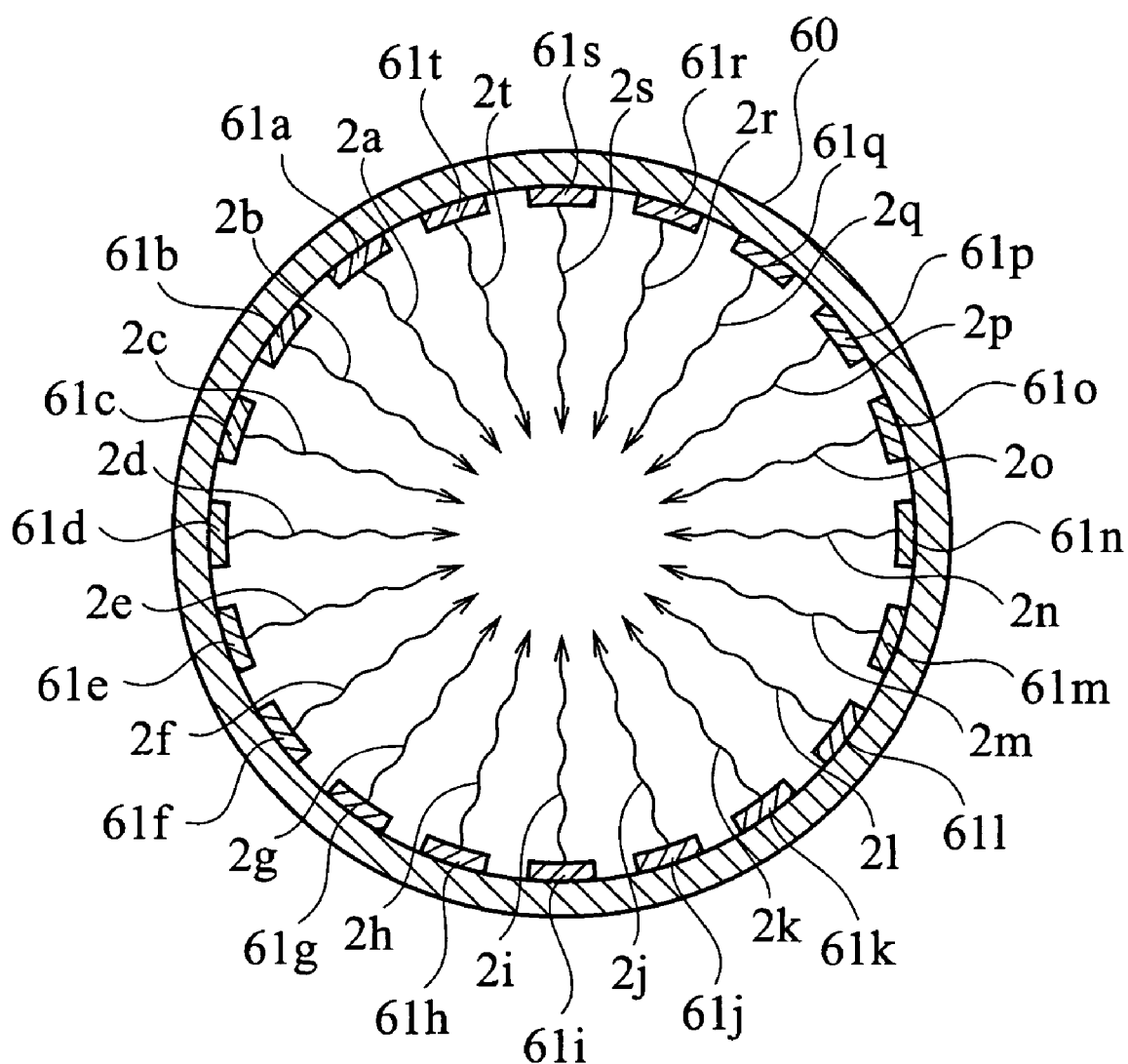
FIG. 10 is a cross sectional view of the antenna array taken on plane A-A in FIG. 9, according to the second embodiment of the present invention.
Figure 11:
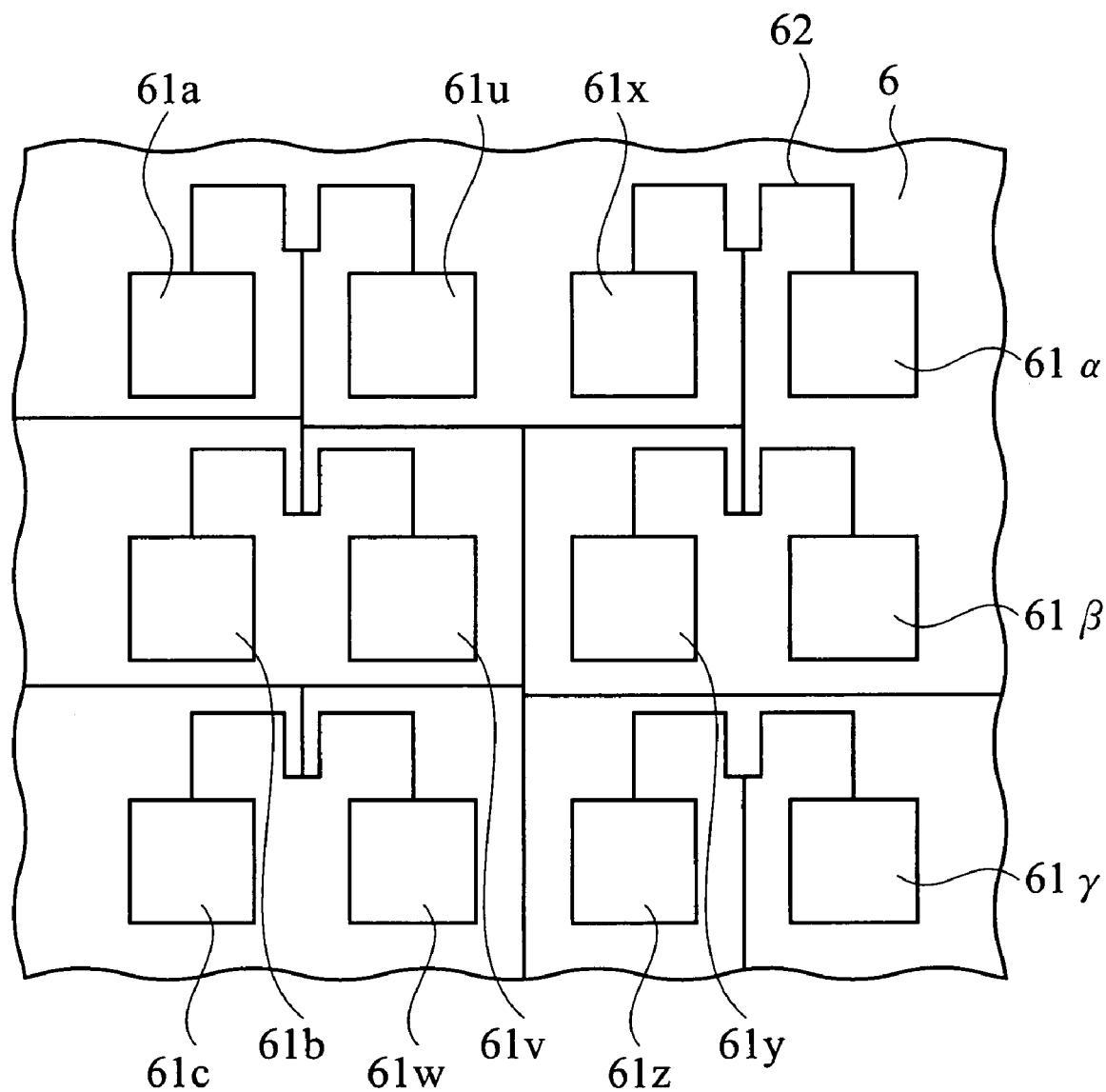
FIG. 11 is a schematic configuration showing an inner wall side of antenna array according to the second embodiment of the present invention.

As shown in FIG. 9, an electromagnetic wave irradiation tool according to a second embodiment of the present invention is medical equipment encompassing an antenna-supporting member 60, a plurality of antennas (the patch antennas) 61a, 61b, 61c, . . . provided on a wall surface of the antenna-supporting member 60, and an electromagnetic wave generation unit 3 configured to supply an electromagnetic wave 2, which has a frequency equal to the characteristic frequency of the subject microorganism (causative agent) 11, to the antennas 61a, 61b, 61c, . . . . The antenna-supporting member 60 and the plural the patch antennas 61a, 61b, 61c, . . . , implement an antenna array 6. The antenna-supporting member 60 has a cylinder-shaped geometry so that and a biological body 1 can lie in the inside of the cylinder. As shown in FIG. 10, a plurality of the patch antennas 61a, 61b, 61c, . . . , 61t are arranged in the inner wall of the antenna-supporting member 60 in a matrix-shape. The plural the patch antennas 61a, 61b, 61c, . . . , 61t are respectively connected to a high frequency transmission line 62 as shown in FIG. 11, and are connected to a frequency adjustment device 4 and an electromagnetic wave generation device 5 shown in FIG. 9. The electromagnetic waves generated in the electromagnetic wave generation device 5 are emitted as the electromagnetic wave 2 as shown in FIG. 10 toward the center of antenna array 6 from the patch antennas 61a, 61b, 61c, . . . , 61t. As the high frequency transmission line 62, a coaxial cable, a strip line, a coplanar waveguide can be used. Other structure and materials are similar to the configuration already shown in FIG. 1, and overlapping or redundant description may be omitted in the second embodiment. In addition, in FIG. 9, although the antenna-supporting member 60 is represented as a large-scale antenna-supporting member 60 accommodating the whole of a human body, but even smaller cylinder, which accommodates only arm or leg portion, is preferable. Furthermore, the antenna-supporting member 60 may have a size, which accommodates only one finger.

A procedure of medical treatment using the electromagnetic wave irradiation tool according to the second embodiment of the present invention will be described.

(a) At first, in FIG. 9, the medical-care site such as necrosis or boil (swelling) that occurred on skin of the biological body 1 is specified so as to measure the characteristic frequency of the subject microorganism (causative agent) 11 existing in the medical-care site. Similar to the measurement method explained in the first embodiment, the characteristic frequency may be determined beforehand, by Raman spectroscopy, or by measuring VSWR of the subject microorganism 11 through a reflection-ratio measuring instrument.

(b) Next, as shown in FIG. 9, the biological body 1 is lied on a bed 63, and the biological body 1 is inserted in the inside of the antenna-supporting member 60.

(c) Next, the electromagnetic wave generation device 5 generates an electromagnetic wave having a frequency near to the characteristic frequency of the subject microorganism 11 in the biological body. For example, the electromagnetic wave generation device 5 generates the electromagnetic wave 2 of one THz to 100 THz, and the frequency adjustment device 4 adjusts the frequency to become equal to the characteristic frequency of the subject microorganism 11. Next, the patch antennas 61a, 61b, 61c, . . . , 61t, which are provided on the inner wall of antenna array 6, irradiate electromagnetic waves 2a, 2b, 2c, . . . , 2t to the biological body 1. The subject microorganism 11 living in the biological body 1 are excited by the energy of electromagnetic waves 2a, 2b, 2c, . . . , 2t, which have a resonance frequency of the subject microorganism 11 so as to cause a resonance, and the cell membrane is destroyed, or alternatively, the cell division stops. On the other hand, normal cell of the biological body 1 is not excited to the resonance state, because the normal cell has a different characteristic frequency from the subject microorganism 11, and the destruction or the stop of cell division of the normal cell is not caused.

According to the electromagnetic wave irradiation tool related to the second embodiment of the present invention, electromagnetic waves 2a, 2b, 2c, . . . , 2t having a frequency different from the characteristic frequency of the normal cell, but equal to the characteristic frequency of the microorganism are irradiated on the biological body 1 from the patch antennas 61a, 61b, 61c, . . . , 61t disposed in the inner wall of the antenna supporting member 60 in a matrix-shape. Then, only the microorganism is oscillated to bring into the resonant state, without damaging the normal cell, so that a specified microorganism is selectively oscillated until the specified microorganism is destroyed.

In the electromagnetic wave irradiation tool shown in FIG. 9, before interposing the biological body 1, for example, in the inside of the antenna-supporting member 60, it is preferable to provide a shield on part which is not an object of the medical treatment. In addition, it is preferable to control a power level of the electromagnetic wave depending on the depth from the surface of the biological body 1 at the medical treatment site. Or a switch may be established in each of the patch antennas 61a, 61b, 61c, ..., 61t so that the electromagnetic waves 2a, 2b, 2c, ..., 2t can be emitted selectively from specific the patch antennas 61a, 61b, 61c, ..., 61t.

Generally, when an electromagnetic wave is irradiated on a tissue of the biological body 1, because the energy of the electromagnetic wave is absorbed by the tissue, as the electromagnetic wave propagates in the tissue, a phenomenon of gradual attenuation of the electromagnetic wave must be considered. When the tissue of the biological body 1 is considered as a dielectric, attenuation constant γ for the electromagnetic wave propagating in the tissue is expressed in the next equation:

$$\gamma = j\omega(\in\mu)^{1/2}\{1-j(\sigma/\omega\in)\}^{1/2} \qquad (2)$$

In Eq. (2), σ is conductivity of the tissue, ∈ is dielectric constant of the tissue, μ is permeability of the tissue, ω is angular frequency of the electromagnetic wave. Because a value of p=σ/ω∈ is known to be approximately 0.1<p<10 in a biological tissue, when the real part of the Eq. (2) is defined as α, the next equation is provided:

$$\alpha = \omega[(\mu\in/2)\{(1+p^2)^{1/2}-1\}]^{1/2}] \qquad (3)$$

When, in the Eq. (3), if we consider the case in which the frequency f is high:

$$\alpha = \omega\{(\mu\in/2)p\}^{1/2} \qquad (4)$$

The level of penetration of the electromagnetic wave in the tissue is expressed by the depth δ at which the power density of the electromagnetic wave is reduced by $e^{-2}$. And δ is given by a reciprocal oF α, and referred as "skin depth" or "penetration depth" of the electromagnetic wave. Because, in Eq. (4), δ=1/α:

$$\delta(1/\pi f\mu\sigma)^{1/2} \qquad (5)$$

is obtained as an approximate expression. It can supposed that $\in_r \approx 1$[F/m], $\mu_r \approx 80$[H/m], because the biological body has a dielectric constant approximately equal to the dielectric constant of water, and most of the molecules composing the biological body 1 can be regarded as non-magnetic materials. The dielectric constant and permeability in vacuum are $\in_0 \approx 8.8542\times10^{-12}$ [F/m], $\mu_0 \approx 4\pi \times 10^{-7}$ [H/m], respectively. In the electromagnetic wave irradiation tool shown in FIG. 9, employing Eq. (5), the penetration depth δ is given approximately as δ=70 micrometers when the electromagnetic wave having a frequency of 3 THz is irradiated on the tissue, and the penetration depth δ is given approximately as δ=115 micrometers when the electromagnetic wave having a frequency of 1.2 THz. In addition, the penetration depth δ is given approximately as δ=231 micrometers when the electromagnetic wave having a frequency of 300 GHz is irradiated, according to the data of skin of a rabbit at 23 GHz measured by Gandhi et. al and the data calculated by equations of complex dielectric constant based on Debye relaxation.

As explained above, when a high frequency electromagnetic wave having a frequency higher than microwave band is irradiated, it is found that the penetration depth of the electromagnetic wave arrives at a neighborhood region of the body surface. In the electromagnetic wave irradiation tool shown in FIG. 9, it is preferable to medical treat the biological body 1 in which the microorganism is parasitic in a neighborhood of epidermis. In the electromagnetic wave irradiation tool related to the second embodiment of the present invention, an electromagnetic wave having a frequency less than or equal to one THz can be employed. Namely, by irradiating an electromagnetic wave having a low frequency of around dozens of kHz against chromosomes in a cell, for example, so as to oscillate the chromosome, it is possible to suppress the cell division.

In addition, in view of the situation that there are a plurality of characteristic frequencies in a specified microorganism, the electromagnetic wave generation unit 3 may encompass a plurality of electromagnetic wave generation devices 5, similar to the first embodiment, so that electromagnetic waves having different frequencies can be simultaneously emitted.

Third Embodiment

An electromagnetic wave irradiation tool according to a third embodiment of the present invention is medical equipment encompassing a blood irrigation system 9 having a blood-draw line 93 configured to draw blood from the biological body 1 and a blood-return line 94 configured to return the blood to the biological body 1, an electromagnetic wave irradiation unit (antenna array) 6 configured to irradiate an electromagnetic wave having a frequency equal to the characteristic frequency of a microorganism (causative agent) existing in the blood in the blood-draw line 93, and an electromagnetic wave generation unit 3 configured to supply the electromagnetic wave to the electromagnetic wave irradiation unit (antenna array) 6. The configuration of the electromagnetic wave generation unit 3 is similar to the configuration already explained in FIG. 1, and overlapping or redundant description may be omitted in the third embodiment.

Figure 12:
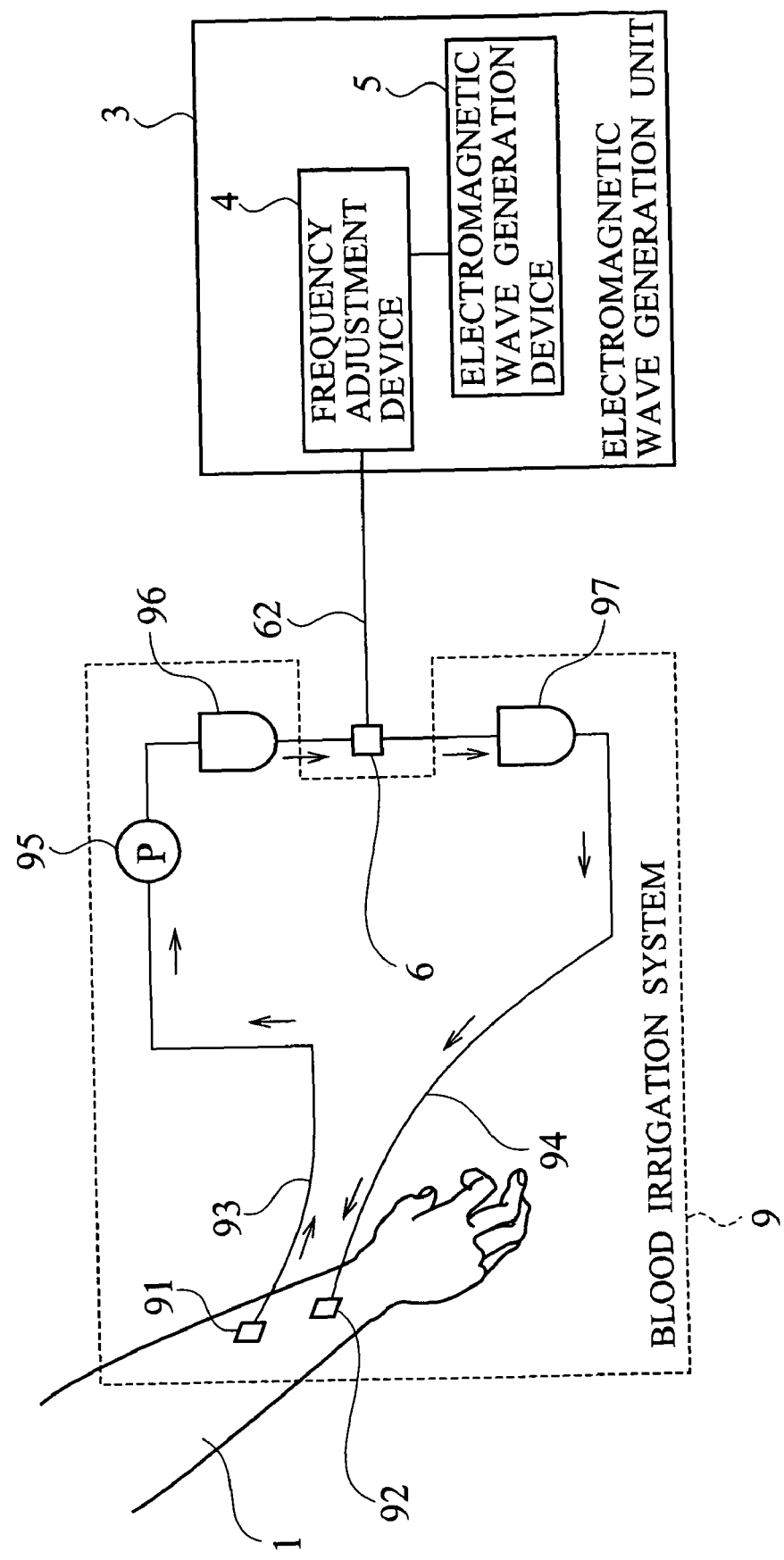
FIG. 12 is a schematic configuration showing an electromagnetic wave irradiation tool according to a third embodiment of the present invention.
Figure 13:
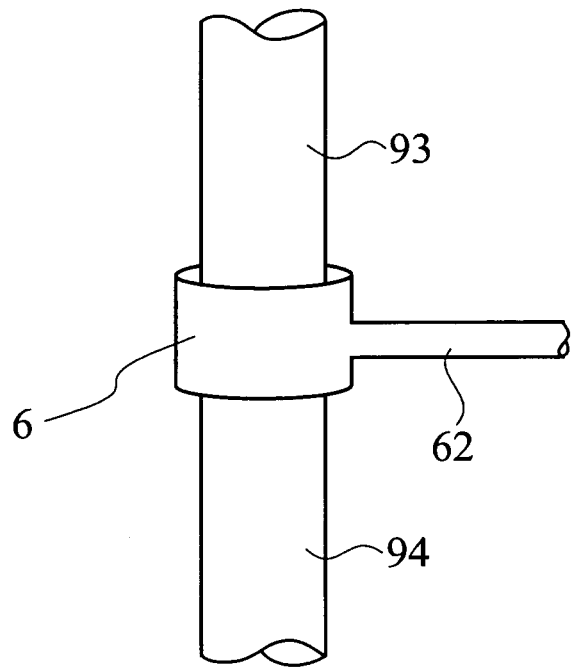
FIG. 13 shows an enlarged view of the electromagnetic wave irradiation tool according to the third embodiment of the present invention.
Figure 14:
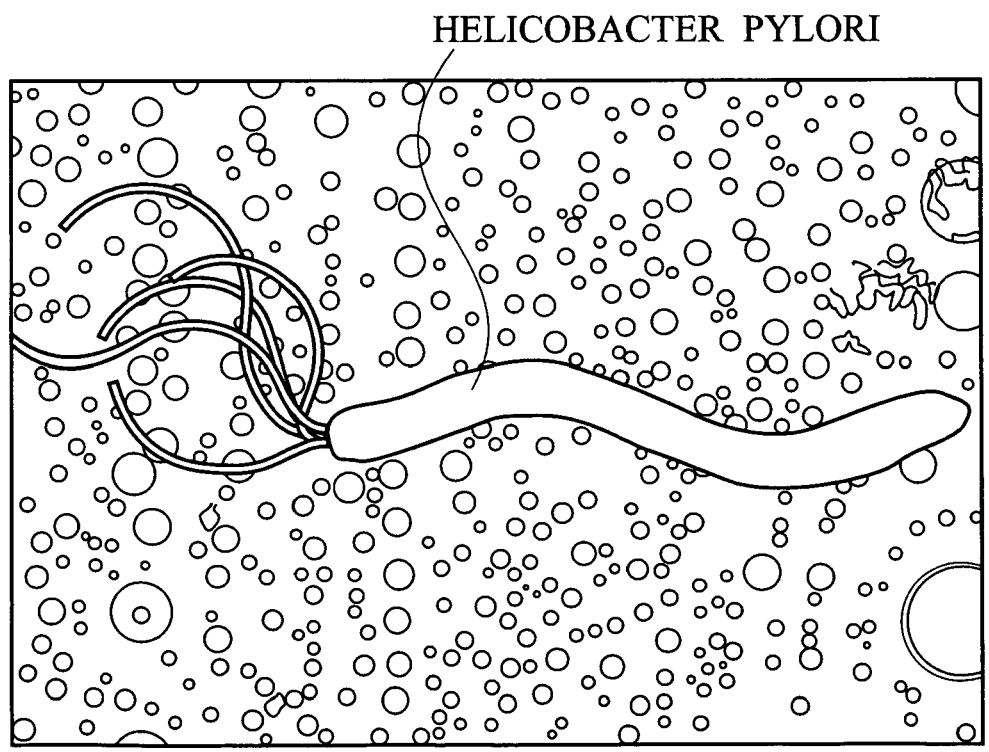
FIG. 14 shows a schematic illustration of *helicobacter pylori*.

As shown in FIG. 12, the blood irrigation system 9 has the blood-draw line 93, the antenna array 6 provided on the down stream side of the blood-draw line 93, and the blood-return line 94 provided on the down stream side of antenna array 6. The blood-draw line 93 has a blood drawing terminal 91, a blood pump 95 provided on the down stream side the blood drawing terminal 91, a chamber 96 provided on the down stream side the blood pump 95. The blood-return line 94 has a chamber 97 provided on the down stream side of the antenna array 6 and a blood returning terminal 92 provided on the down stream side of the chamber 97. The blood-draw line 93 and the blood-return line 94 are formed of silicon tube. As shown in FIG. 13, the electromagnetic wave irradiation unit (antenna array) 6 surrounds the circumference of the tubes of the blood-draw line 93 and the blood-return line 94. The configuration of the antenna array 6 is equivalent to a configuration explained in FIGS. 10 and 11, in which the inside diameter and the length are miniaturized, while keeping the same structure, such that a plurality of patch antennas (not shown) are arranged in the inner wall in a matrix-shape, and the patch antennas surrounds the entire outer circumference of the tube of the blood-draw line 93 and the blood-return line 94. As shown in FIG. 12, the antenna array 6 is connected to the frequency adjustment device 4 and the electromagnetic wave generation device 5 through the high frequency transmission line 62. The outer diameter of the tube equal to or smaller than 140 micrometers is preferred, because the penetration depth δ of the electromagnetic wave of three THz in blood is given approximately as δ=70 micrometers, as already explained. By a bundled up structure implemented a plurality of tubes, each having an outside diameter equal to or smaller than 140 micrometers, electromagnetic waves can be irradiated to each tube by the electromagnetic wave irradiation units 6 attached to each tubes, while assuring blood flow of a large quantity. Or, alternatively with a tube of honeycomb structure implemented by a plurality of bores, each having an inside diameter of approximately 2δ, the patch antennas may be established in the inner wall of each of the bores. Because it is not realistic, if the inside diameter of the tubes becomes too narrow, it is preferable to meander the tube having an inside diameter larger than 2δ so that blood passing in the center of the tube may collide to the inner wall of the tube at plural times.

Next, a procedure of medical treatment using the electromagnetic wave irradiation tool according to the third embodiment of the present invention will be described with reference to FIG. 12.

(a) At first, the blood drawing terminal 91 punctures an artery of the biological body 1, and a vein of the biological body 1 is punctured by the blood returning terminal 92. From the blood drawing terminal 91 blood of the biological body 1 is collected, and transported to the chamber 96 through the blood pump 95. The blood that air and foreign substances are removed by the chamber 96 flows into the side to which the antenna array 6 is arranged.

(b) Next, an electromagnetic wave generation device 5 generates an electromagnetic wave having a frequency equal to the characteristic frequency of the microorganism living in blood, and through the frequency adjustment device 4 and the high frequency transmission line 62, the electromagnetic wave is supplied to the antenna array 6. The antenna array 6 to which the electromagnetic wave is supplied irradiates the electromagnetic wave to the blood from the circumferences of the tubes of the blood-draw line 93 and the blood-return line 94. Because kinetic energy is given, the microorganism in the blood, to which the electromagnetic wave is irradiated, is driven to a state of resonant vibration, and the destruction of a cell membrane, or the stop of cell division occurs. On the other hand, a normal cell in blood is not excited, because the normal cell has a different characteristic frequency from the microorganism cell, and the destruction of the normal cell is not produced.

In addition, by collecting blood of the biological body 1 beforehand so as to measure the characteristic frequency of the subject microorganism or the subject abnormal cell with Raman scattering spectrometry, the frequency of the electromagnetic wave to be irradiated from the antenna array 6 can be determined by.

According to the third embodiment of the present invention, the microorganism existing in blood is excited selectively so as to destroy the microorganism, without damaging a normal cell in blood.

In addition, similar to the first and second embodiments, the electromagnetic wave generation unit 3 may encompass a plurality of electromagnetic wave generation devices 5, so that electromagnetic waves having different frequencies can be simultaneously emitted.

Other Embodiments

As explained above, the present invention is described by means of the first to third embodiments, the statement of disclosure or the drawings should not be understood as limiting the invention. Various modifications or alternate embodiments will become possible for those skilled in the art after receiving the teaching of the present disclosure.

In the first embodiment already explained, a laparoscope can be employed instead of the endoscope probe 7. In this case, at three or four sites, small incisions of 5-20 mm are made in the skin of the biological body 1, and surgical instrument such as a long exclusive forceps or scissors and the narrow tube (laparoscope) 7 are inserted percutaneously in the biological body 1, while projecting on a viewing screen of the monitor 86 the transmitted images of the internal structure of the biological body 1, and the electromagnetic wave can be irradiated in the biological body 1. The electromagnetic wave irradiation terminal 74 is not required to be provided at the tip of the endoscope probe 7, and the electromagnetic wave irradiation terminal 74 may be provided at the tip of another narrow tube, resembling the shape of the endoscope probe 7. Furthermore, the electromagnetic wave irradiation terminal 74 may be provided at the tip of surgical instrument such as forceps. The frequency of the electromagnetic wave 2 being irradiated from the electromagnetic wave irradiation terminal 74 can be measured, by providing a frequency-detecting terminal at the tip of the endoscope probe 7.

In the third embodiment, it may be configured such that blood cells in blood contain drug, while irradiating the electromagnetic wave to blood from the antenna array 6.

The electromagnetic wave irradiation tool according to the third embodiment of the present invention can be implement by miniaturized total chemical analysis systems (μ-TAS), which merges a plurality of micro-apparatuses in a single chip. That is to say, using a structure of μ-TAS, bloods are led precisely to various narrow tubes by means of pressure from a syringe pump so that healthy blood is carried away from a fluid circuit, while blood affected by microorganism is collected to a micro-reactor, and the electromagnetic wave having a frequency equal to the characteristic frequency of the microorganism is irradiated to the blood affected by the microorganism. Furthermore, in addition to blood, a group of cells may be transported along with a Ringer's solution so that a healthy cell is drained from a fluid circuit, while a cell affected by microorganism is collected to a micro-reactor, and the electromagnetic wave having a frequency equal to the characteristic frequency of the microorganism is irradiated to the cell affected by the microorganism. "A Ringer's solution" is a liquid including ions of sodium, potassium, calcium and chlorine, which is used for keeping a cell in living state outside the biological body 1, the cell is extracted from the biological body 1 in order to hold. In this case, an actuator substrate of the μ-TAS is implemented by a silicon substrate, a glass substrate, a ceramic substrate such as an alumina ($Al_2O_3$) substrate, or a polymer substrate. On the top surface of the actuator substrate, a cell-injecting reservoir configure to store temporary a group of cells with the Ringer's solution, and a drain reservoir configure to store temporary the group of cells, to which a scheduled processing has been over, before the group of cells are exhausted, are provided. Between the cell-injecting reservoir and the drain reservoirs, a plurality of fluid paths (micro-fluid paths) are provided, each of the fluid paths has a width of one micrometer to several hundred micrometers, preferably several micrometers to several ten micrometers, and a depth of one micrometer to several hundred micrometers, preferably several micrometers to several ten micrometers, so that the group of cells separated and collected from the biological body 1 can be transported through the fluid paths (micro-fluid paths) with the Ringer's solution. The μ-TAS is further implemented by an entrance side micro-valve, an entrance side micro-pump, which are arranged in the fluid path, in a neighborhood of the cell-injection reservoir, and an exit side micro-valve disposed in the fluid path in front of the drain reservoir. As the entrance side micro-valve and the exit side micro-valve, various kinds of micro-valves such as diaphragm type (membrane type), piezoelectric device type, electrostatic type, an electromagnetic valve type or bimetal/shape-memory alloy type can be employed. As the entrance side micro-pump, various kinds of micro-pumps such as piezoelectric device type, electrostatic type, an electromagnetic valve type or bimetal/shape-memory alloy type can be employed. Furthermore, a micro-pump using a change of specific volume by thermal expansion, or alternatively using a change of specific volume by temperature dependence of the saturated vapor pressure in fluid and by a phase change ascribable to the application of heat, a micro-pump which apply a magnetic field to magnetic fluid, or an electro-hydro-dynamical (EHD) pump using a specific interaction between fluid and electric field generated in the fluid by application of high electric field can be employed.

In the first to third embodiments, zinc telluride (ZnTe) or lithium niobate (LiNbO$_3$) may be used instead of GaP for the core layer of the electromagnetic wave generation device 5. The electromagnetic wave 2 emitted from the electromagnetic wave generation device 5 may be generated by parametric oscillation. In addition, in the first to third embodiments, before medically treating the biological body 1 by the electromagnetic wave, drug such as photosensitive materials may be administered to the biological body 1 so as to facilitate specifying the existing position of the subject microorganism (causative agent). As means for specifying the existing site of the microorganism, a magnetic resonance imaging (MRI) equipment, a photo-topography equipment, a functional MRI (FMRI) equipment, and an infrared computer tomographic (CT) imaging equipment may be used together. An abnormal cell, caused by parasitism of the microorganism, or by mutation of a cell, can be medically treated by irradiating electromagnetic wave having a frequency equal to the characteristic frequency of the abnormal cell.

In addition, in the first to third embodiments, although a case that a single electromagnetic wave generation unit 3 has a plurality of electromagnetic wave generation devices 5 in the inside the electromagnetic wave generation unit 3 was described, the electromagnetic wave irradiation tool of the present invention can be implemented by a plurality of electromagnetic wave generation units 3. In this case, the plural electromagnetic wave generation units 3 provide oscillations of plural frequencies, simultaneously.

Furthermore, the electromagnetic wave generation devices 5 explained in the first to third embodiments may be connected to or installed in an air cleaner of air-conditioner so as to irradiate the electromagnetic wave having a frequency equal to the characteristic frequency of virus such as influenza virus floating in the air, or the electromagnetic wave having a frequency equal to the characteristic frequency of methicillin-resistant Staphylococcus aureus (MRSA), so that the virus or the pathogenic bacteria lose their multiplication/infection capability. To be concrete, patch antennas 61$a$, 61$b$, 61$c$, ... 61$t$, similar to the configuration shown in FIGS. 9 and 10, may be installed in an air cleaner of air-conditioner. In addition, because protein is destroyed in a molecule level at the surface of these microorganisms by irradiating the electromagnetic wave having a frequency equal to the characteristic frequency of coxsackie virus, which is one of a cause of "summer cold", MRSA, which is said to be a representative cause of nosocomial infection (hospital infection), *Escherichia coli* and black mold (*Aspergillus*), the electromagnetic wave irradiation tool of the present invention facilitates a microorganism extermination technology in the atmosphere.

As pathogenic substances of food poisoning, bacteria, virus, chemical compound, and natural poison, etc. are known, but more than 80% of cause of food poisoning is ascribable to bacteria. For example, in Japan, enteritis vibrio is a representative food poisoning-causing bacteria ranking with *Salmonella*, and the occurrence frequency of the food poisoning due to enteritis vibrio is the highest in food poisoning-causing bacteria of intra toxin (toxin produced in biological body by multiplication of bacteria) type. Because enteritis vibrio prefers seawater with the most preferred habitation place, in the summer when temperature of seawater rises, enteritis vibrios are multiplied flourishingly so as to pollute marine and fishery products with high frequency. The human being who has eaten the polluted seafood develops symptoms of diarrhea, stomachache, pyrexia or vomiting, or alternatively dies in a case. For example, if the patch antennas 61$a$, 61$b$, 61$c$, ..., 61$t$, as shown in FIGS. 9 and 10 are provided in the inside of a refrigerator, in the inside of a food-preserving box or above a kitchen table, with a electromagnetic wave irradiation unit configured to irradiate an electromagnetic wave having a frequency equal to the characteristic frequency of the food poisoning-causing bacteria, the food poisoning-causing bacteria can be killed selectively.

In this way the present invention includes inherently the various embodiments, which are not described here. Therefore, technical scopes of the present invention are prescribed only by the description of claims, being proper from the above explanation.

INDUSTRIAL APPLICABILITY

Because the term "biological body" means a living body of a creature, every animals and plants conducting vital phenomena are included in the term "biological body". In particular, in a biological body of animal classified into any of chondrichthyes, osteichthyes, amphibia, reptilia, aves and mammalia in vertebrate, the present invention can be applied to a medical treatment of a cell to which microorganism is parasite, or alternatively to a medical treatment of an abnormal cell, which is affected by mutation of a cell. For example, if the characteristic frequency of the avian corona-virus (infectious bronchitis virus), the surface structure of which agrees with severe-acute-respiratory syndrome (SARS) virus, avian corona-virus is classified into the same family and the same genus as SARS virus, is measured beforehand, SARS virus can be extirpated selectively. Furthermore, the electromagnetic wave irradiation tool of the present invention can be can be employed as medical equipment in the field of these medical care. Because the microorganism parasitic on a plant can be exterminated selectively, the electromagnetic wave irradiation tool of the present invention can be can be applied to industrial fields of agriculture and food processing. Furthermore, the electromagnetic wave irradiation tool of the present invention can be can be applied to an industrial field of air cleaners such as air-conditioners.

The invention claimed is:

1. An electromagnetic wave irradiation tool comprising:
   a cylindrical narrow tube configured to be inserted in a biological body, including:
      an electromagnetic wave irradiation terminal that irradiates an electromagnetic wave of terahertz band having a frequency equal to a characteristic frequency of a cell of an inner portion of the biological body at the top end of the narrow tube so as to excite the cell by the electromagnetic wave emitted from the electromagnetic wave irradiation terminal, and
      a high frequency transmission line embedded in the narrow tube, configured to transmit the electromagnetic wave to the electromagnetic wave irradiation terminal from the bottom end of the narrow tube; and
   an electromagnetic wave generation unit configured to generate the electromagnetic wave and to supply the electromagnetic wave to the high frequency transmission line.

2. The electromagnetic wave irradiation tool of claim 1, wherein the narrow tube further comprises a temperature detecting unit embedded in the narrow tube, configured to detect temperature of the cell.

3. The electromagnetic wave irradiation tool of claim 1, wherein the electromagnetic wave generation unit irradiates simultaneously electromagnetic waves having different frequencies.

4. The electromagnetic wave irradiation tool of claim 1, wherein the electromagnetic wave generation unit generates the electromagnetic wave of one THz to 100 THz.

5. The electromagnetic wave irradiation tool of claim 1, wherein the cell is an abnormal cell, caused by parasitism of microorganism, or by mutation.

6. The electromagnetic wave irradiation tool of claim 5, wherein the electromagnetic wave generation unit adjusts the frequency to a resonance frequency of the abnormal cell so as to cause selectively a resonance state of the abnormal cell, so that normal cells around the abnormal cell are not excited by the electromagnetic wave.

7. An electromagnetic wave irradiation tool comprising:
a cylindrical narrow tube configured to be inserted in a biological body, including:
an electromagnetic wave irradiation terminal that irradiates an electromagnetic wave of terahertz band having a frequency equal to a characteristic frequency of a cell of an inner portion of the biological body at the top end of the narrow tube so as to excite the cell by the electromagnetic wave emitted from the electromagnetic wave irradiation terminal,
a high frequency transmission line embedded in the narrow tube, configured to transmit the electromagnetic wave to the electromagnetic wave irradiation terminal from the bottom end of the narrow tube, and
a frequency adjustment device embedded in the narrow tube, configured to adjust the frequency of the electromagnetic wave being irradiated to the cell so as to follow a change of the characteristic frequency; and
an electromagnetic wave generation unit configured to generate the electromagnetic wave and to supply the electromagnetic wave to the high frequency transmission line.

8. An electromagnetic wave irradiation tool comprising:
an antenna-supporting member;
a plurality of antennas provided on the antenna-supporting member; and
a blanched high frequency transmission line that delivers an electromagnetic wave of terahertz band having a frequency equal to a characteristic frequency of a cell of biological body to each of the plurality of antennas; and
an electromagnetic wave generation unit configured to supply the electromagnetic wave to the high frequency transmission line so as to excite the cell by the electromagnetic wave emitted from the plurality of antennas.

9. The electromagnetic wave irradiation tool of claim 8, wherein the electromagnetic wave generation unit irradiates simultaneously continuous electromagnetic waves having different frequencies.

10. The electromagnetic wave irradiation tool of claim 8, wherein the electromagnetic wave generation unit generates the electromagnetic wave of one THz to 100 THz.

11. The electromagnetic wave irradiation tool of claim 8, wherein the cell is an abnormal cell, caused by parasitism of microorganism, or by mutation.

12. The electromagnetic wave irradiation tool of claim 11, wherein the electromagnetic wave generation unit adjust the frequency to a resonance frequency of the abnormal cell so as to cause selectively a resonance state of the abnormal cell, so that normal cells around the abnormal cell are not excited by the electromagnetic wave.

13. An electromagnetic wave irradiation tool comprising:
an antenna-supporting member;
an antenna provided on the antenna-supporting member; and
an electromagnetic wave generation unit that supplies a continuous electromagnetic wave having a frequency equal to a characteristic frequency of a cell of biological body,
wherein the electromagnetic wave generation unit further comprises a frequency adjustment device configured to adjust the frequency of the continuous electromagnetic wave being irradiated to the cell so as to follow a change of the characteristic frequency.

14. An electromagnetic wave irradiation tool comprising:
a blood irrigation system including:
a blood-draw line configured to draw blood from a biological body, and
a blood-return line configured to return the blood to the biological body;
an electromagnetic wave irradiation unit that irradiates an electromagnetic wave of terahertz band having a frequency equal to a characteristic frequency of a cell of biological body existing in the blood in the blood-draw line so as to excite the cell by the electromagnetic wave; and
an electromagnetic wave generation unit configured to supply the electromagnetic wave to the electromagnetic wave irradiation unit.

15. The electromagnetic wave irradiation tool of claim 14, wherein the electromagnetic wave generation unit irradiates simultaneously electromagnetic waves having different frequencies.

16. The electromagnetic wave irradiation tool of claim 14, wherein the electromagnetic wave generation unit generates the electromagnetic wave of one THz to 100 THz.

17. The electromagnetic wave irradiation tool of claim 14, wherein the cell is an abnormal cell, caused by parasitism of microorganism, or by mutation.

18. The electromagnetic wave irradiation tool of claim 17, wherein the electromagnetic wave generation unit adjusts the frequency to a resonance frequency of the abnormal cell so as to cause selectively a resonance state of the abnormal cell, so that normal cells around the abnormal cell are not excited by the electromagnetic wave.

19. An electromagnetic wave irradiation tool comprising:
a blood irrigation system having:
a blood-draw line configured to draw blood from a biological body, and
a blood-return line configured to return the blood to the biological body;
an electromagnetic wave irradiation unit that irradiates a continuous electromagnetic wave having a frequency equal to a characteristic frequency of a cell of biological body existing in the blood in the blood-draw line; and
an electromagnetic wave generation unit configured to supply the continuous electromagnetic wave to the electromagnetic wave irradiation unit,
wherein the electromagnetic wave generation unit further comprises a frequency adjustment device configured to adjust the frequency of the continuous electromagnetic wave being irradiated to the cell so as to follow a change of the characteristic frequency.

* * * * *